(12) United States Patent
Assell et al.

(10) Patent No.: US 9,345,488 B2
(45) Date of Patent: May 24, 2016

(54) METHOD OF CUTTING TISSUE

(71) Applicant: ZYGA TECHNOLOGY, INC., Minnetonka, MN (US)

(72) Inventors: Robert Assell, St. Paul, MN (US); Jeremy Carr, Lauderdale, MN (US); Eugene Dickhudt, Lino Lakes, MN (US); Thomas Berg, Centerville, MN (US); Brian Beaubien, St. Paul, MN (US)

(73) Assignee: Zyga Technology, Inc., Minnetonka, MN (US)

( * ) Notice: Subject to any disclaimer, the term of this patent is extended or adjusted under 35 U.S.C. 154(b) by 0 days.

(21) Appl. No.: 14/728,227

(22) Filed: Jun. 2, 2015

(65) Prior Publication Data
US 2015/0257770 A1    Sep. 17, 2015

Related U.S. Application Data

(62) Division of application No. 13/734,743, filed on Jan. 4, 2013, now Pat. No. 9,113,919, which is a division of application No. 12/938,976, filed on Nov. 3, 2010, now Pat. No. 8,348,950.

(60) Provisional application No. 61/292,021, filed on Jan. 4, 2010.

(51) Int. Cl.
| | |
|---|---|
| *A61B 17/16* | (2006.01) |
| *A61B 19/00* | (2006.01) |
| *A61B 17/32* | (2006.01) |
| *A61B 17/3203* | (2006.01) |
| *A61B 17/70* | (2006.01) |
| *A61B 17/00* | (2006.01) |
| *A61B 17/3207* | (2006.01) |

(52) U.S. Cl.
CPC ......... *A61B 17/1617* (2013.01); *A61B 17/1664* (2013.01); *A61B 17/1671* (2013.01); *A61B 17/32002* (2013.01); *A61B 17/320016* (2013.01); *A61B 17/1604* (2013.01); *A61B 17/1608* (2013.01); *A61B 17/3203* (2013.01); *A61B 17/7055* (2013.01); *A61B 2017/0046* (2013.01); *A61B 2017/00261* (2013.01); *A61B 2017/00867* (2013.01); *A61B 2017/320004* (2013.01); *A61B 2017/32006* (2013.01); *A61B 2017/320012* (2013.01); *A61B 2017/320028* (2013.01); *A61B 2017/320032* (2013.01); *A61B 2017/320791* (2013.01)

(58) Field of Classification Search
CPC ........... A61B 17/1617; A61B 17/1664; A61B 17/32002; A61B 17/320016
See application file for complete search history.

(56) References Cited

U.S. PATENT DOCUMENTS

| | | | | | |
|---|---|---|---|---|---|
| 5,015,255 | A | * | 5/1991 | Kuslich | A61B 17/1671 128/898 |
| 5,242,444 | A | * | 9/1993 | MacMillan | A61B 17/1757 606/60 |

(Continued)

*Primary Examiner* — Christian Sevilla
(74) *Attorney, Agent, or Firm* — Michael A. Bondi; Moss & Barnett

(57) ABSTRACT

A method of cutting tissue between a first bone and a second bone. An aperture is formed through the first bone. The aperture has a radius. An undercutting system is provided. The undercutting system includes a cutter. The undercutting system is extended into the aperture. The cutter is moved with respect to the undercutting system to an extended configuration where at least a portion of the cutter extends from the undercutting system. The cutter is used to cut tissue between the first bone and the second bone that is beyond the radius of the aperture. The undercutting system is removed from the aperture.

23 Claims, 24 Drawing Sheets

(56) References Cited

U.S. PATENT DOCUMENTS 5,591,170 A * 1/1997 Spievack .......... A61B 17/14 30/122

5,928,239 A * 7/1999 Mirza .......... A61B 17/1668 606/167

2008/0114364 A1 * 5/2008 Goldin .......... A61B 17/1617 606/79

* cited by examiner

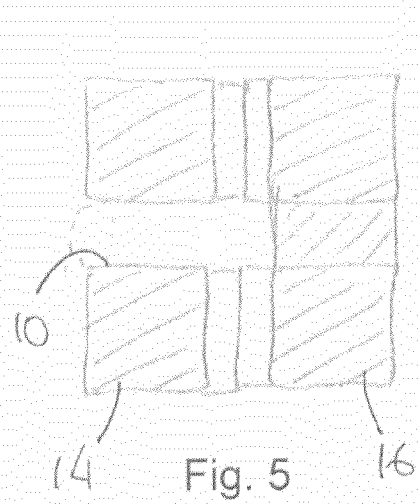
Fig. 5
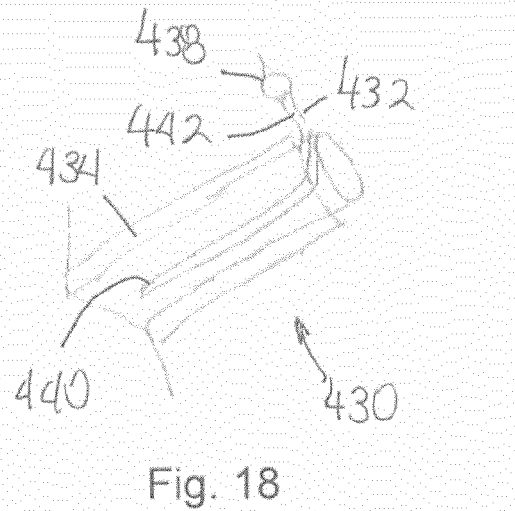
Fig. 18
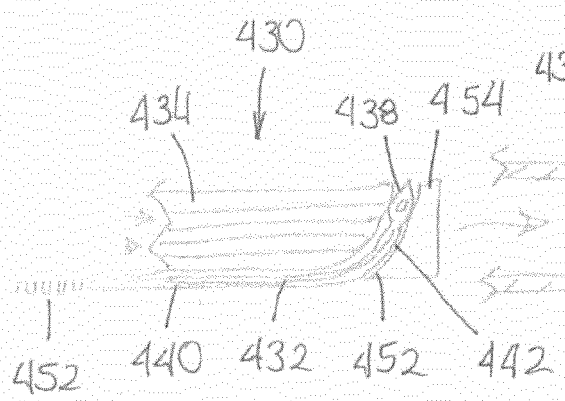
Fig. 19
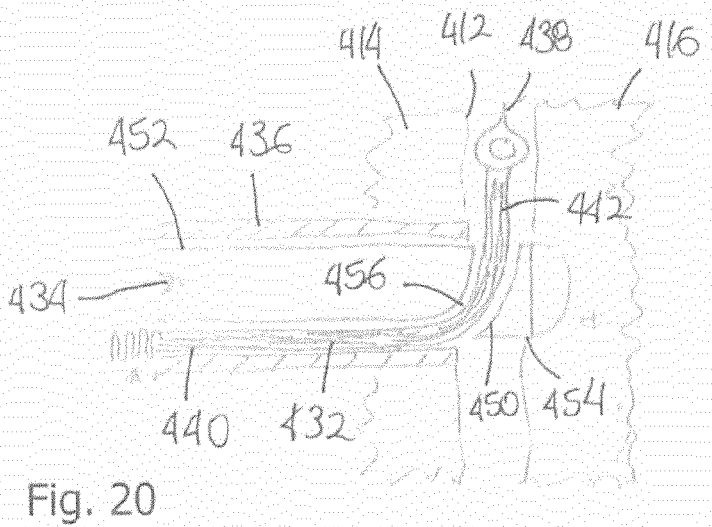
Fig. 20

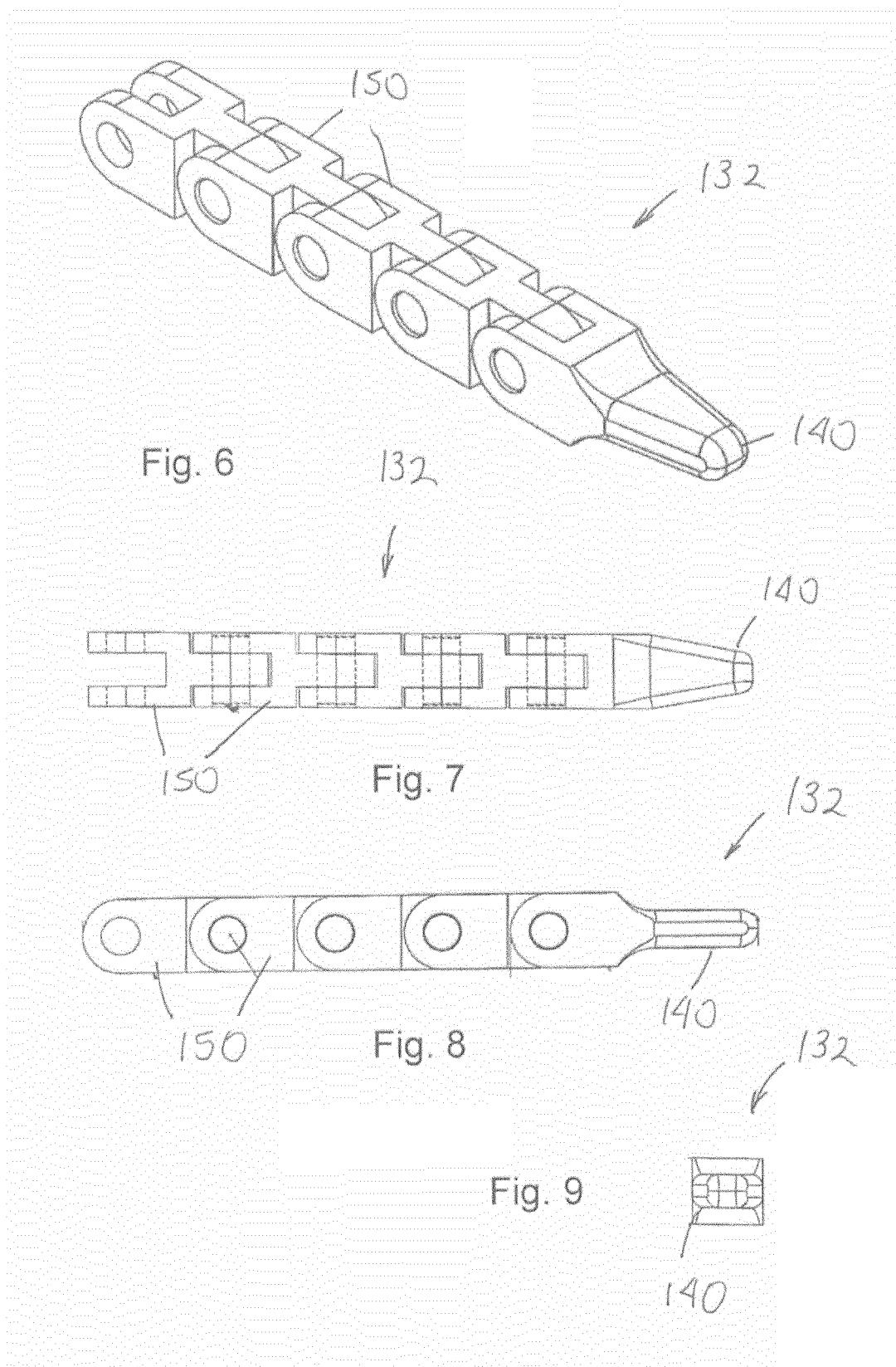

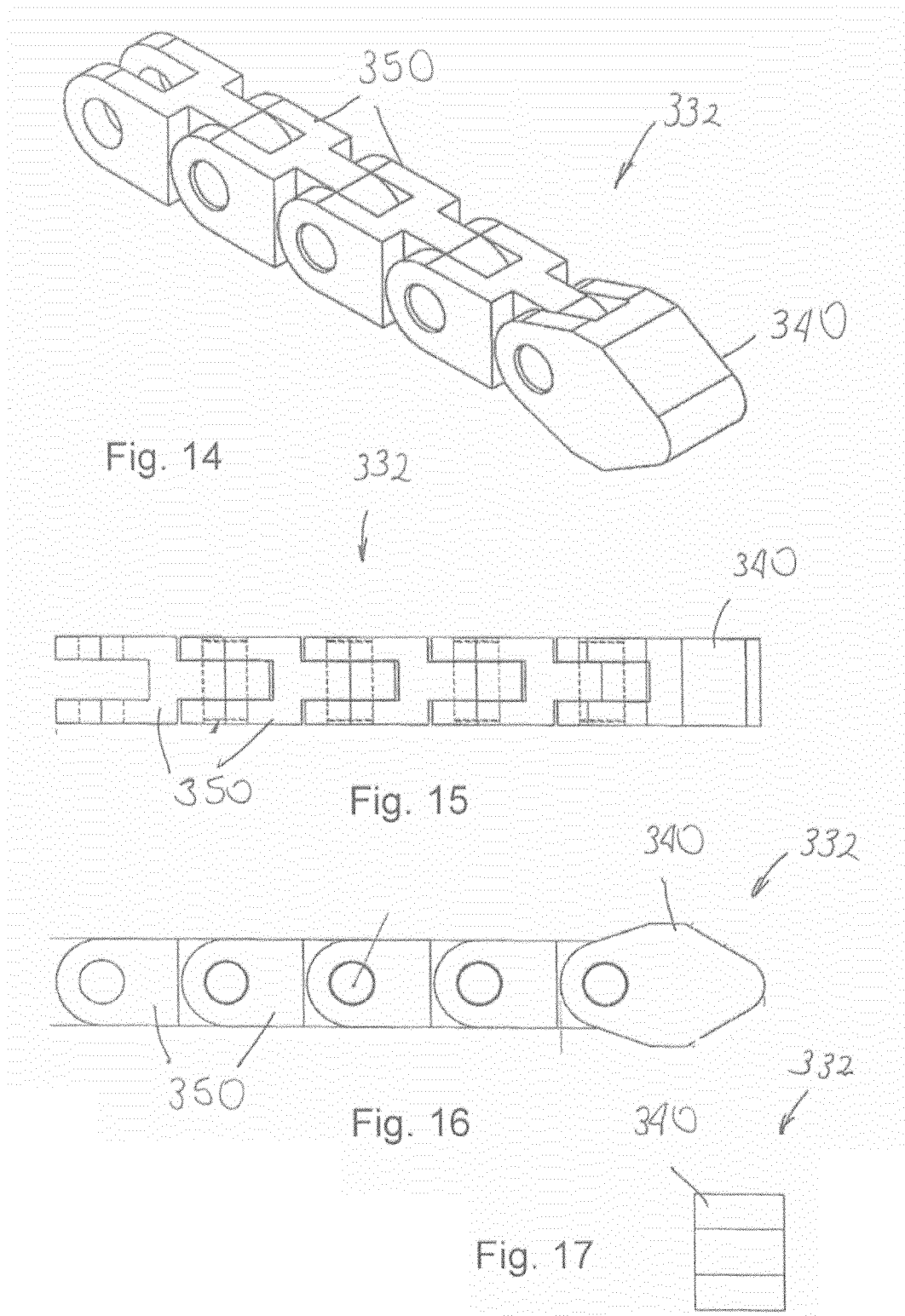

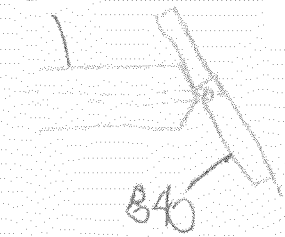
Fig. 48
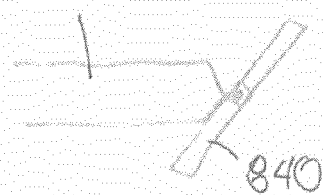
Fig. 49
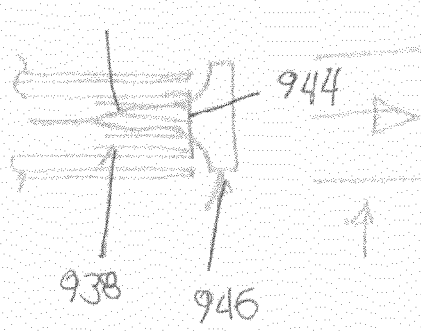
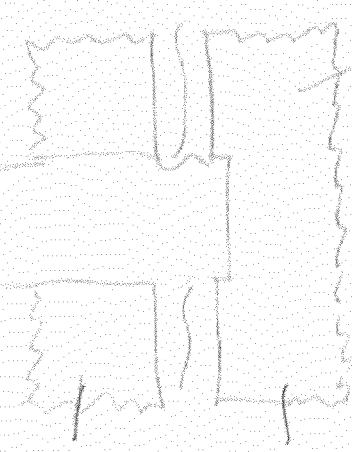
Fig. 50
Fig. 51
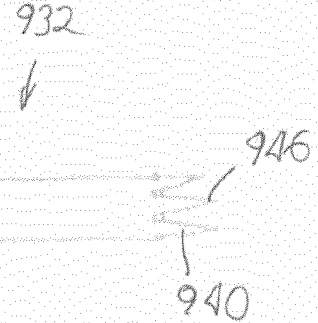
Fig. 52

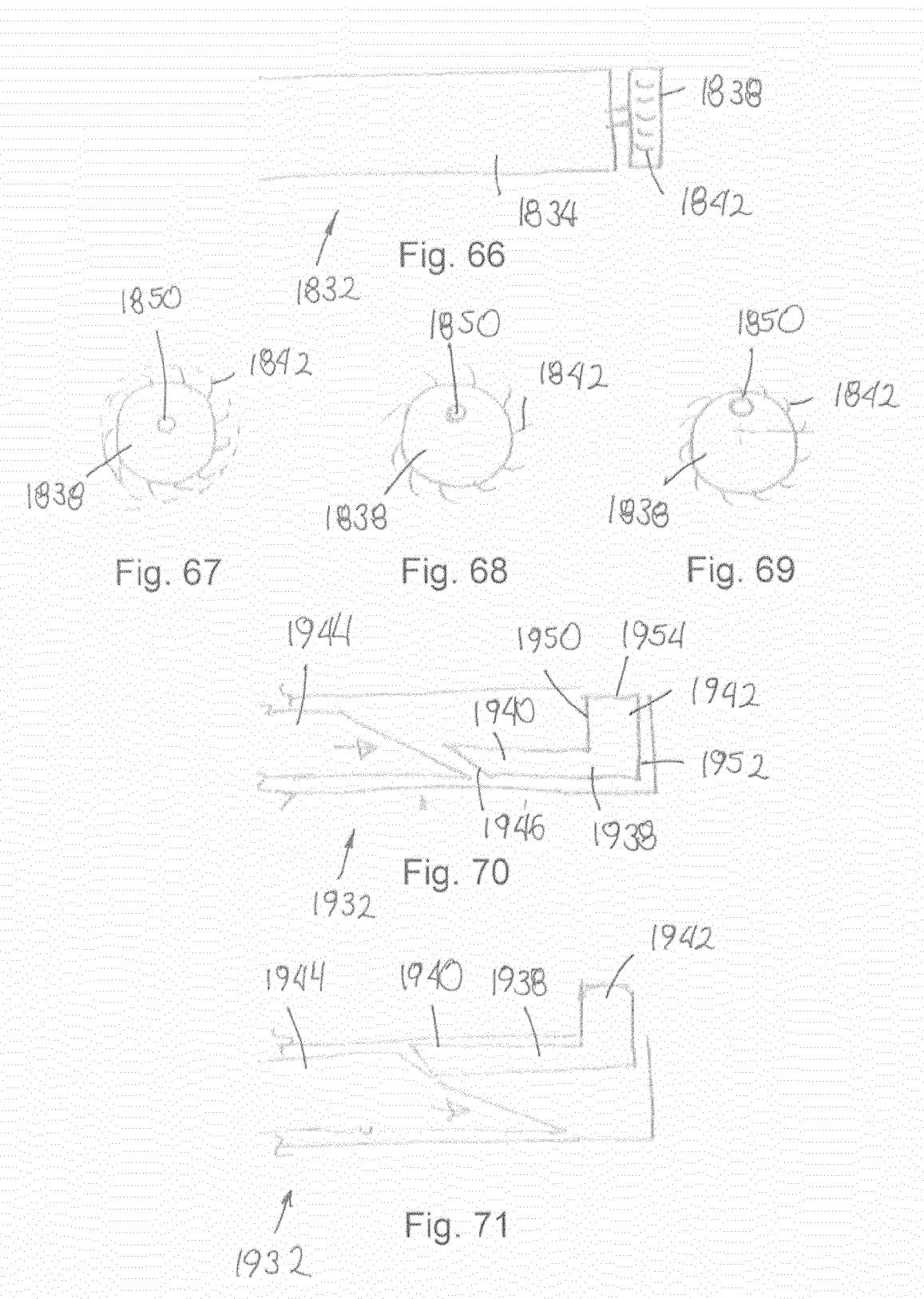

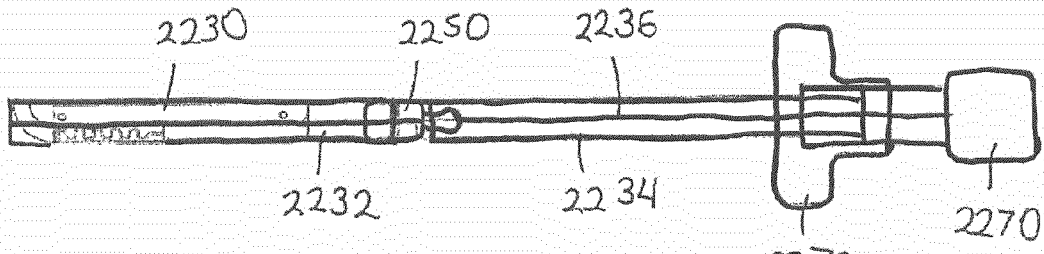
Fig. 76
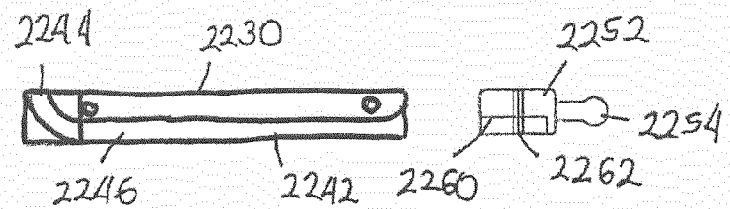 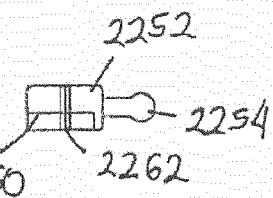
Fig. 77  Fig. 78
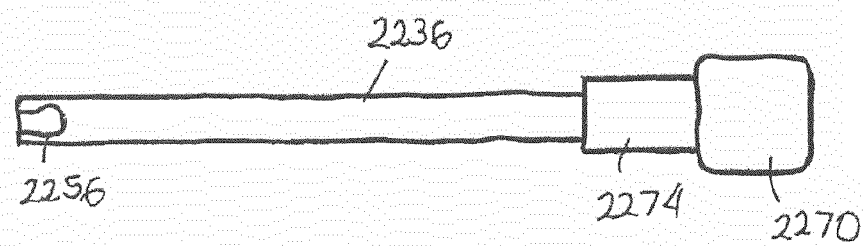
Fig. 79
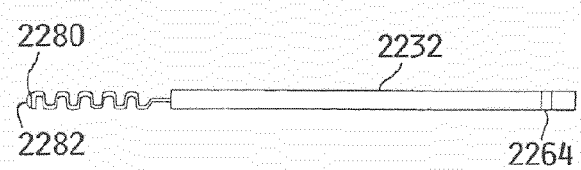 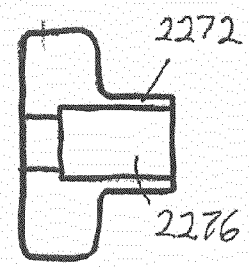
Fig. 80  Fig. 81

METHOD OF CUTTING TISSUE

REFERENCE TO RELATED APPLICATION

This application is a divisional of U.S. application Ser. No. 13/734,743, which was filed on Jan. 4, 2013, which is a divisional of U.S. application Ser. No. 12/938,976, which was filed on Nov. 3, 2010, and this application claims priority to U.S. Provisional Application No. 61/292,021, which was filed on Jan. 4, 2010, the contents of which are incorporated herein by reference.

FIELD OF THE INVENTION

An embodiment of the invention is directed to a system for treating patients experiencing sacroiliac joint pain. More particularly, the invention relates to a system for preparing a space between the sacrum and the iliac to facilitate sacroiliac joint fusion.

BACKGROUND OF THE INVENTION

The sacroiliac joint is located at the intersection of the ilium, the upper bone of the pelvis, and the sacrum at the base of the spine. One of the primary functions of the sacroiliac joint is to provide shock absorption of pressures put on the spine.

Certain persons experience pain in the sacroiliac joint. This pain may result from a variety of causes, examples of which include injuries, incorrect vertebra fusion during pre-birth development and effects of pregnancy.

If initial efforts to reduce the pain in the sacroiliac joint through physical therapy and/or steroid injections are not effective, surgery may be needed to fuse together the sacroiliac joint. One typical surgical technique involves forming an incision in the lower back over the sacroiliac joint. The articular cartilage is removed from both surfaces. This process is also called chondrectomy.

The sacrum and the ilium are held together with screws or a plate. Eventually, bone grows between the sacrum and the ilium to thereby fuse together the sacroiliac joint. Because of the challenges in accessing the surfaces of the sacrum and the ilium that will fuse together, this type of surgery may result in damage to tissue, nerves and/or blood vessels that surround the sacroiliac joint. Such damage may prevent the patient from fully realizing the benefits of the sacroiliac joint fusion and in some instances cause the patient to experience more pain after the sacroiliac joint fusion than before the sacroiliac joint fusion.

SUMMARY OF THE INVENTION

An embodiment of the invention is directed to a method of cutting tissue between a first bone and a second bone. An aperture is formed through the first bone. The aperture has a radius. An undercutting system is provided. The undercutting system includes a cutter. The undercutting system is extended into the aperture. The cutter is moved with respect to the undercutting system to an extended configuration where at least a portion of the cutter extends from the undercutting system. The cutter is used to cut tissue between the first bone and the second bone that is beyond the radius of the aperture. The undercutting system is removed from the aperture.

Another embodiment of the invention is directed to a method of cutting tissue between a first bone and a second bone. An aperture is formed through the first bone. The aperture has a radius. An undercutting system is provided. The undercutting system includes an insertion apparatus and a cutter operably attached to the insertion apparatus. The insertion apparatus has a central axis. The undercutting system is extended into the aperture. The cutter with is moved respect to the undercutting system to an extended configuration where at least a portion of the cutter extends from the undercutting system. When the cutter is in the extended configuration, a distal end of the cutter is further from the central axis than when the cutter is in a retracted configuration. The cutter is used to cut tissue between the first bone and the second bone that is beyond the radius of the aperture. The undercutting system is removed from the aperture.

Another embodiment of the invention is directed to a method of cutting tissue between a first bone and a second bone. An aperture is formed through the first bone. The aperture has a radius. An undercutting system is provided. The undercutting system includes a cutter. The undercutting system is extended into the aperture. The cutter is moved with respect to the undercutting system to an extended configuration where at least a portion of the cutter extends from the undercutting system. The cutter is used to cut tissue between the first bone and the second bone that is beyond the radius of the aperture. The undercutting system is removed from the aperture. The cut tissue is removed from between the first bone and the second bone. Bone graft material is inserted between the first bone and the second bone from where the cut tissue has been removed.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5 is a sectional view of the sacroiliac joint with an aperture formed in the ilium.

FIG. 6 is a perspective view of an end portion of a probe assembly for use with the undercutting system.

FIG. 7 is a top view of the end portion of the probe assembly of FIG. 6.

FIG. 8 is a side view of the end portion of the probe assembly of FIG. 6.

FIG. 9 is an end view of the end portion of the probe assembly of FIG. 6.

FIG. 14 is a perspective view of an end portion of a cutting assembly for use with the undercutting system.

FIG. 15 is a top view of the end portion of the cutting assembly of FIG. 14.

FIG. 16 is a side view of the end portion of the cutting assembly of FIG. 14.

FIG. 17 is an end view of the end portion of the cutting assembly of FIG. 14.

FIG. 18 is a sectional view of an undercutting system for use in conjunction with sacroiliac fusion in a partially extended configuration.

FIG. 19 is a sectional view of the undercutting system of FIG. 18 positioned adjacent to an undercutting guide that has been inserted into the aperture formed in the ilium where a cutting assembly is in a retracted configuration.

FIG. 20 is a sectional view of the undercutting system of FIG. 18 positioned between the sacrum and the ilium where the cutting assembly is in an extended configuration.

FIG. 48 is a side view of the cutting head of FIGS. 46 and 47 in a first articulated position.

FIG. 49 is a side view of the cutting head of FIGS. 46 and 47 in a second articulated position.

FIG. 50 is a sectional view of another alternative undercutting system positioned adjacent to an undercutting guide that has been inserted into the aperture formed in the ilium where a cutting head is in a retracted position.

FIG. 51 is a perspective view of the undercutting system of FIG. 50 where the cutting head is in an extended position.

FIG. 52 is a side view of an alternative configuration of the cutting head for the undercutting system of FIG. 50.

FIG. 66 is a sectional view of an alternative configuration of the undercutting system.

FIG. 67 is an end view of a cutting head for use with the undercutting system of FIG. 66.

FIG. 68 is an end view of another cutting head for use with the undercutting system of FIG. 67.

FIG. 69 is an end view of another cutting head for use with the undercutting system of FIG. 67.

FIG. 70 is a sectional view of an alternative configuration of the undercutting system where the undercutting system is in a retracted configuration.

FIG. 71 is a sectional view of the undercutting system of FIG. 70 where the undercutting system is in an extended configuration.

FIG. 76 is a sectional view of an alternative configuration of the undercutting system where a cutting assembly is in a retracted configuration.

FIG. 77 is a side view of a cutting assembly guide for the undercutting system of FIG. 76.

FIG. 78 is a side view of a connector head for the undercutting system of FIG. 76.

FIG. 79 is a side view of an advancement handle for the undercutting system of FIG. 76.

FIG. 80 is a side view of a cutting assembly for the undercutting system of FIG. 76.

FIG. 81 is a side view of a rotation handle for the undercutting system of FIG. 76.

DETAILED DESCRIPTION OF THE PREFERRED EMBODIMENTS

Figure 1:
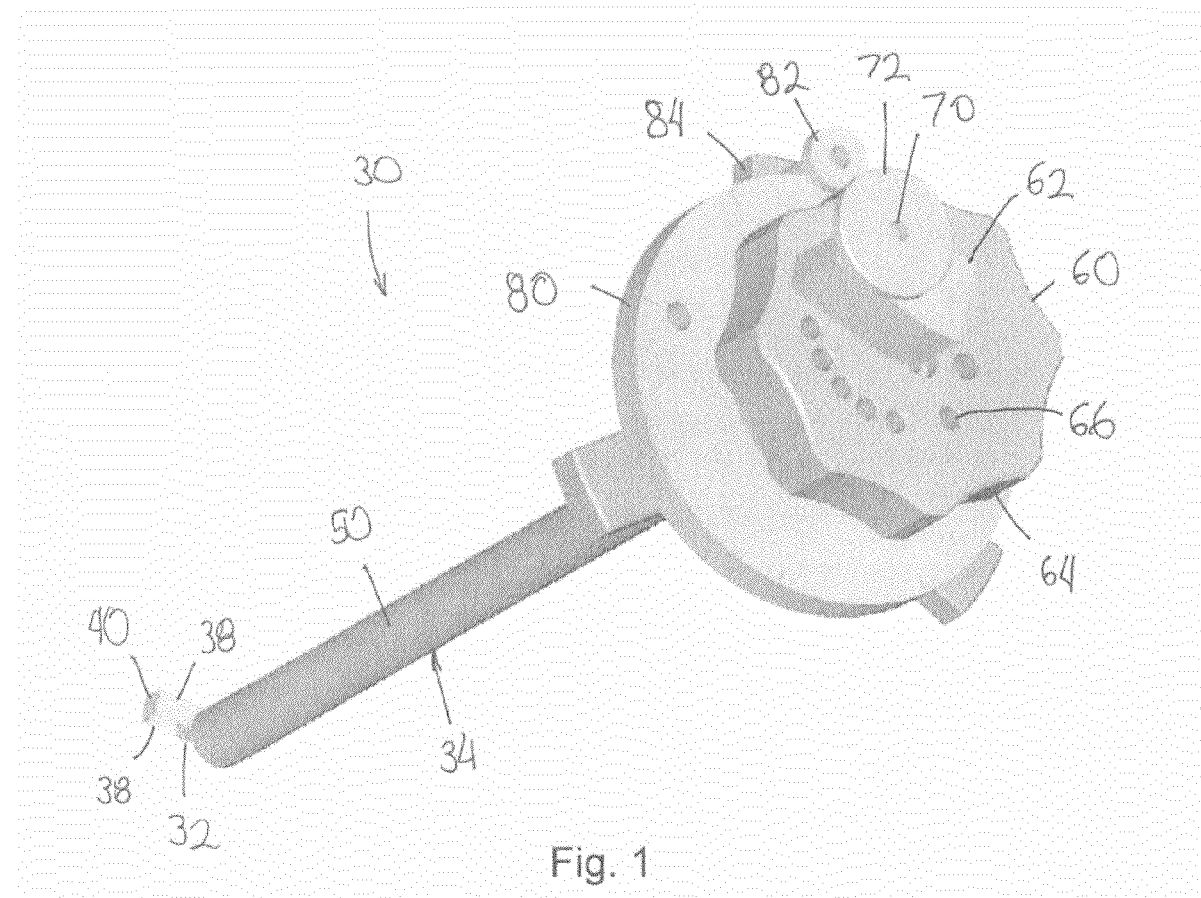
FIG. 1 is a perspective view of an undercutting system for use in a sacroiliac fusion procedure.

An embodiment of the invention is directed to an undercutting system 30 for preparing surfaces of the ilium and the sacrum for sacroiliac joint fusion, such as is illustrated in FIGS. 1-4. The undercutting system utilizes an aperture 10 formed in the ilium 14 to access a region 12 between the ilium 14 and the sacrum 16, as illustrated in FIG. 5.

In certain embodiments, the aperture 10 may have a diameter of up to about 50 millimeters. In other embodiments, the aperture 10 may have a diameter of between about 6 millimeters and 20 millimeters.

The undercutting system thereby enables tissue such as cartilage to be removed from the adjacent surfaces of the ilium 14 and the sacrum 16. This procedure may be referred to as preparing bleeding bone surfaces on the ilium 14 and the sacrum 16, which are more receptive to growing bone between them as part of sacroiliac joint fusion. Thereafter, the ilium 14 and the sacrum 16 may be held in a stationary position with respect to each other so that bone may grow between the ilium 14 and the sacrum 16 to thereby fuse the sacroiliac joint.

Performing the sacroiliac fusion using the undercutting system 30 disclosed herein reduces the complexity of the sacroiliac fusion when compared to prior techniques used for sacroiliac fusion. Additionally, sacroiliac fusion performed using the concepts describe herein has the potential of fewer side effects because it does not require the surgeon to work proximate the nerves and/or blood vessels, as is done with prior sacroiliac fusion techniques.

Furthermore, the apparatus and technique disclosed herein does not formally expose the sacroiliac joint to reduce the potential of infection. The time associated with preparing the surfaces of the ilium and the sacrum is also reduced when compared to the prior more invasive techniques used to prepare the joint for fusion.

In one embodiment, the undercutting system 30, may include a cutting assembly 32 that is operably mounted with respect to an insertion apparatus 34, as illustrated in FIGS. 1-4. The cutting assembly 32 may have a U-shaped configuration where the ends of the cutting assembly 32 are operably attached to the insertion apparatus 34.

The configuration of the cutting assembly 32 provides the cutting assembly 32 with sufficient rigidity in a radial direction. Such a configuration allows the cutting assembly 32 to resist deformation in response to rotation of the undercutting system 30 during the cutting process such as when the tissue between the ilium 14 and the sacrum 16 is contacted with the cutting assembly 32.

The configuration of the cutting assembly 32 also provides the cutting assembly 32 with flexibility in a distal—proximal direction. Such a configuration allows the cutting assembly 32 to deflect in response to encountering resistance in the distal—proximal direction. The resistance enables the cutting assembly 32 to deflect in response to changes in the shape or orientation of the ilium 14 or the sacrum 16. Such deflection is important because it is much more difficult to cut through the bone of the ilium 14 and the sacrum 16 than the cartilage that is between the ilium 14 and the sacrum 16.

The cutting assembly 32 may be formed with a length that is no greater than a diameter of the elongated shaft 50. Forming the cutting assembly 32 with such a configuration enables the cutting assembly 32 to be positioned substantially within a profile of the elongated shaft 50 when the cutting assembly 32 is in a retracted configuration so that the cutting assembly 32 does not interfere with the insertion of the tool through the aperture in the ilium 14.

The cutting assembly 32 may include a cutting surface 38 on at least one edge thereof. In certain embodiments, cutting surfaces 38 are provided on the upper and lower edges on both sides of the cutting assembly 32. Providing the cutting surfaces 38 on these edges enables the cutting assembly 32 to cut while being rotated in clockwise and counter clockwise directions. Providing the cutting surfaces 38 on these edges also enables the cutting assembly 32 to cut on the ilium 14 and the sacrum 16 sides of the cutting assembly 32.

In certain embodiments, a distal end 40 of the cutting assembly 32 does not have a cutting surface on the edges thereof. Forming the distal end 40 with cutting surfaces on the edges thereof enables the cutting assembly to resist cutting too strongly into the ilium 14, the sacrum 16 or the cartilage between the ilium 14 and the sacrum 16.

The insertion apparatus 34 may include an elongated shaft 50 that is formed with a length that enables a proximal end thereof to be position outside of the patient's body while a distal end thereof is utilized to the prepare the region between the ilium 14 and the sacrum 16 for the fusion process. In certain embodiments, the length of the elongated shaft 50 is between about 6 inches and about 18 inches.

The elongated shaft 50 may be formed with a relatively small outer diameter to reduce a size of the aperture that is formed in the ilium 14. The larger the aperture that is formed in the ilium 14, the greater the potential of the aperture weakening to the point at which the ilium 14 is more susceptible to breakage. In certain embodiments, the outer diameter of the elongated shaft 50 is between about 6 millimeters and 20 millimeters.

The insertion apparatus 34 may include a control portion 52 that facilitates extension and retraction of the cutting assembly 32 as well as rotation of the cutting assembly 32. In certain embodiments, the extension and retraction of the cutting assembly 32 are controlled utilizing a plate 60 and a handle 62 that is operably mounted with respect to the plate.

Figure 3:
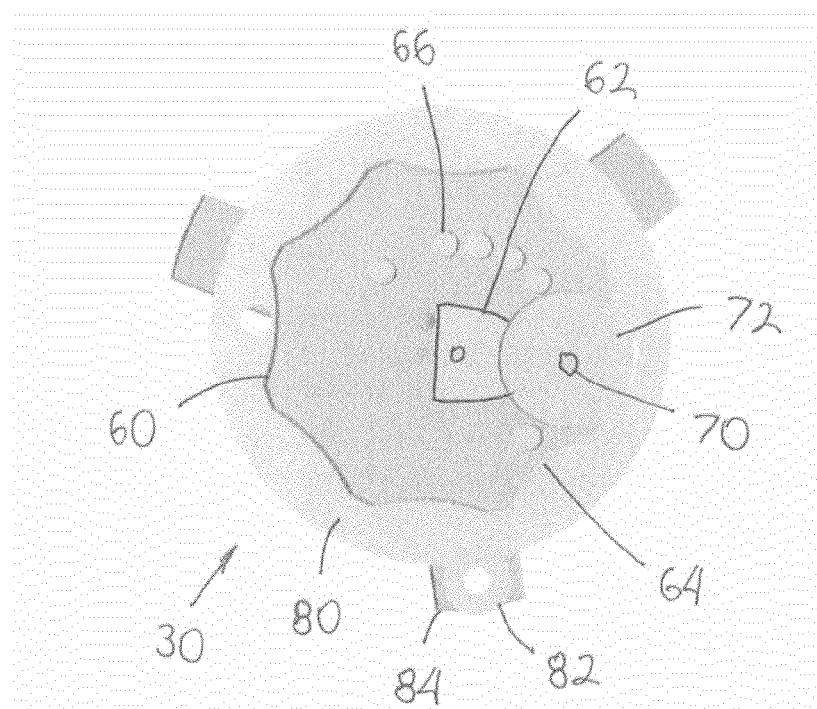
FIG. 3 is a first end view of the undercutting system of FIG. 1.

The plate 60 may have a generally circular configuration, as most clearly illustrated in FIG. 3. An outer edge of the plate 60 may have a plurality of recesses 64 formed therein that enhance a person's ability to grasp the plate 60 to either maintain the plate 60 in a desired position or to rotate the plate 60. The recesses 64 may each have a concave configuration.

The plate 60 may include a plurality of recesses 66 formed in an upper surface thereof. The recesses 66 extend at least partially between the upper surface and the lower surface of the plate. The recesses 66 may be oriented in a semi-circular configuration about an axis. This axis may be offset from a central axis of the plate 60.

A spacing between at least some of the adjacent recesses 66 may be substantially equal. On the other hand, the spacing between adjacent recesses 66 may get progressively larger, as illustrated in FIG. 3.

The handle 62 may be rotatable mounted to the plate 60 for rotation about an axis that is the same as the axis about which the semi-circular configuration of the recesses 66 is oriented. Rotation of the handle 62 causes the cutting assembly 32 to be rotated with respect to the elongated shaft 50 to move the cutting assembly 32 between an extended configuration and a retracted configuration depending on which direction the handle 62 is rotated.

The handle 62 may be operably connected to the cutting assembly 32 such that rotation of the handle 62 causes rotation of the cutting assembly 32. One potential mechanism for operably connecting the handle 62 and the cutting assembly 32 is a shaft (not shown) that extends between the handle 62 and the cutting assembly 32.

The shaft may be rotatable about an axis that is offset from a central axis of the elongated shaft 50. Mounting the shaft in this manner enables the cutting assembly 32 to be fabricated with a length that is approximately the same as a diameter of the elongated shaft 50. This configuration thereby allows the cartilage to be removed from a larger area between the ilium 14 and the sacrum 16 to increase the likelihood that the fusion process will be successful by increasing the area of the fusion between the ilium 14 and the sacrum 16.

It is also possible to include at least one gear between the handle 62 and the cutting assembly 32. The at least one gear may either decrease or increase the amount of movement of the cutting assembly 32 in response to a specified movement of the handle 62.

A locking pin 70 may be operably connected to the handle 62 for movement between a locked configuration and an unlocked configuration. When in the locked configuration, the locking pin 70 extends at least partially into one of the recesses 66 to thereby retain the handle 62 in a fixed position with respect to the plate 60. When in the unlocked configuration, the locking pin 70 does not extend into the recess 66, which enables the handle 62 to be rotated with respect to the plate 60 for extending or retracting the cutting assembly 32 from the elongated shaft 50.

The locking pin 70 may be biased to the locked configuration to prevent inadvertent rotation of the handle 62 to thereby cause unintended extension or retraction of the cutting assembly 32.

A gripping mechanism 72 may be operably attached to the locking pin 70. The gripping mechanism 72 may have a diameter that is great than a diameter of the locking pin 70. The gripping mechanism 72 thereby enhances the ability to move the locking pin 70 from the locked configuration to the unlocked configuration.

The insertion apparatus 34 may also include a rotation control mechanism 80 to facilitate rotation of the cutting assembly 32. In certain embodiments, the rotation control mechanism 80 has a generally circular configuration. A diameter of the rotation control mechanism 80 may be greater than a diameter of the plate 60. Such a configuration enables the rotation control mechanism 80 to be grasped separately from the plate 60.

A lock mechanism 82 may be provided on the insertion apparatus 34 to prevent rotation of the rotation control mechanism 80. At least one arm 84 may extend radially outward from elongated shaft 50 to facilitate attachment of the lock mechanism 82 to the insertion apparatus 34. The arm 84 may have a length that is greater than a length of the radius of the rotation control mechanism 80.

The lock mechanism 82 may be rotatably mounted to the arm 84. Rotation of the lock mechanism 82 with respect to the arm 84 causes a distance between the lock mechanism 82 and the arm 84 to be reduced such that there is frictional contact between the lock mechanism 82 and the rotation control mechanism 80. In certain embodiments, there may also be frictional contact between the arm 84 and the rotation control mechanism 80 when the lock mechanism 80 is in the locked configuration.

In one embodiment of the undercutting system, at least two different cutting assemblies are utilized to prepare the sacroiliac joint for fusion. Using more than one assembly to prepare the sacroiliac joint fusion enhances the accuracy of the preparation process. In such a process, a first cutting assembly 132 (FIGS. 6-9) is used as a probe to define the general region where the sacroiliac joint fusion will take place. A second cutting assembly 232 (FIGS. 10-13) is then used to cut a majority of the tissue from where the sacroiliac joint fusion will take place. A third cutting assembly 332 (FIGS. 14-17) is next used to scrape the bone surfaces where the sacroiliac joint fusion will take place.

As the first cutting assembly 132 is used to define the general region where the sacroiliac fusion will take place, the first cutting assembly 132 may be formed with a distal tip 140 that does not include providing a significant cutting action.

Rather, the distal tip 140 may have a tapered configuration where a width and a height proximate a distal end thereof is less than a width and a height of the plurality of links 150. The tapered configuration enhances the ability of the distal tip 140 to extend through the tissue as opposed to the distal tip 140 having a non-tapered end.

Rather than being sharpened to facilitate cutting into the tissue between the sacrum and the ilium, side edges and a distal end of the distal tip 140 may curved. Such a configuration encourages the distal tip 140 to follow a path of least resistance through the tissue as opposed to digging into the surfaces of the sacrum and the ilium.

The edges of the distal tip 140 in the tapered region may be curved to facilitate the distal tip passing into tissue as opposed to the distal tip 140 cutting through the tissue. Similarly, the distal end may be curved or otherwise shaped with an unsharpened end.

Forming the first cutting assembly 132 with this configuration facilitate extending the first cutting assembly 132 through the tissue while minimizing the potential that the first cutting assembly 132 cuts too deeply into the bone on the sacrum or the ilium. Cutting into the bone too deeply could weaken the bone and potentially inhibit the ability of the undercutting system to prepare the surfaces of both the sacrum and the ilium.

The first cutting assembly 132 may include a plurality of links that are pivotally mounted to each other. The plurality of links 150 provides the first cutting assembly 132 with rigidity along a radial—tangential direction while providing the first cutting assembly 132 with flexibility in a distal—proximal direction. This configuration allows the first cutting assembly 132 to be deflected to a substantially perpendicular orientation after the undercutting guide is inserted while allowing the undercutting system to be rotated to prepare the region for the sacroiliac joint fusion.

The corners of the plurality of links 150 may be sharpened to provide cutting as the undercutting system is rotated. Such cutting caused by the plurality of links 150 will not negatively affect the operation of the undercutting system because the distal tip 140 will have formed a path through the tissue prior to the plurality of links reaching the tissue.

During the process of probing the sacroiliac joint with the first cutting assembly 132, the first cutting assembly 132 may be partially extended from the undercutting guide and then rotate the undercutting guide to form a generally circular path between the sacrum and the ilium. Once the user determines the path is generally clear such as by a reduced resistance to rotation of the undercutting guide, the first cutting assembly 132 may be further extended from the undercutting guide so that a region having a larger radius may be prepared. This process may be repeated until a region having a desired radius is prepared.

The first cutting assembly 132 is then withdrawn from the undercutting guide and the second cutting assembly is inserted into the undercutting guide. When withdrawing the first cutting assembly 132, it is not necessary for the first cutting assembly 132 to be slowly withdrawn by reversing the procedure by which the first cutting assembly 132 is gradually extended into the region between the sacrum and the ilium.

Rather, the undercutting guide may include a mechanism that allows the first cutting assembly to be rapidly withdrawn from the undercutting guide. One such mechanism for quickly removing the first cutting assembly 132 is to provide a button on at least one of the undercutting guide or the first cutting assembly 132 that is movable between an engaged position and a disengaged position. This button mechanism may operate similar to a conventional caulking gun.

When the button is in the engaged position, the first cutting assembly 132 may be advanced slowly such as by rotating a portion of the undercutting guide. When the button is in the disengaged position, the first cutting assembly 132 may slide with respect to the undercutting guide to facilitate quickly removing the first cutting assembly 132 from the undercutting guide 132.

The second cutting assembly 232 is illustrated in FIGS. 10-13 and is used to cut a large portion of the tissue between the sacrum and the ilium to prepare for fusion of the sacroiliac joint. In this regard, the second cutting assembly 232 may include a cutting tip 240 having an elongated configuration with an aperture 242 extending through a central portion thereof. The first and second side surfaces 244 of the cutting tip 240 may have sharpened edges to facilitate the second cutting assembly 232 being used to simultaneously cut tissue from the sacrum and illium sides of the second cutting assembly 232.

An end surface 246 of the cutting tip 240 that extends between the first and second side surfaces 244 may be curved. The end surface 246 of the cutting tip 240 may also include a sharpened edge, which facilitates cutting tissue that is proximate the end. Similar to the first cutting assembly 132, a distal end 246 of the second cutting assembly 232 may not have a sharpened surface to minimize the potential of the second cutting assembly 232 cutting too deeply into the surfaces of the sacrum and the ilium.

Opposite ends of the cutting tip 240 may have sharpened surfaces to facilitate performing cutting when the undercutting guide is rotated in clockwise and counterclockwise directions.

Similar to the first cutting assembly 132, the second cutting assembly 232 may include a plurality of links 250 that are pivotally mounted to each other. The plurality of links 250 provides the second cutting assembly 232 with rigidity along a radial—tangential direction while providing the second cutting assembly 232 with flexibility in a distal—proximal direction. This configuration allows the second cutting assembly 232 to be deflected to a substantially perpendicular orientation after the undercutting guide is inserted while allowing the undercutting system to be rotated to prepare the region for the sacroiliac joint fusion.

During the process of cutting the tissue in the sacroiliac joint with the second cutting assembly 232, the second cutting assembly 232 may be partially extended from the undercutting guide and then rotate the undercutting guide to cut tissue and form a generally circular path between the sacrum and the ilium. Once the user determines the path is generally clear such as by a reduced resistance to rotation of the undercutting guide, the second cutting assembly 232 may be further extended from the undercutting guide so that tissue can be cut from a progressively larger radius. This process may be repeated until a region having a desired radius is prepared.

The second cutting assembly 232 is then withdrawn from the undercutting guide and the third cutting assembly 332 is inserted into the undercutting guide. The third cutting assembly 332 is illustrated in FIGS. 14-17 and is used to further prepare the surfaces of the sacrum and the ilium for fusion of the sacroiliac joint.

The distal tip 340 on the third cutting assembly 332 may have a width that is greater than a width of the distal tip 240 used in conjunction with the second cutting assembly 232. The third cutting assembly 332 thereby facilitates further preparing the surfaces of the sacrum and the ilium by cutting and/or scraping tissue from the sacrum and the ilium.

The distal tip 340 may have a generally diamond shape that enables at least a portion of the distal tip 340 to conform to the surface of the sacrum or the ilium when the distal tip is deflected from an orientation that is substantially aligned with the portions that are adjacent thereto.

An edge surface 342 of the distal tip 340 that extends substantially therearound may be sharpened to facilitate performing a cutting action along both the sacrum and the ilium sides of the distal tip. Additionally, the edge surfaces 342 on opposite sides of the distal tip 340 may be sharpened to facilitate performing a cutting action when the third cutting assembly 332 is rotated in clockwise and counterclockwise directions.

During the process of preparing region between the sacrum and the ilium for the sacroiliac joint fusion, the distal tip of the cutting assembly may extend slowly from the undercutting guide. The undercutting system may include a visual indicator on a region thereof that remains outside the patient during the use thereof. In certain embodiments, at least one of the undercutting guide and the cutting assembly may include a visual indicator that includes a visual representation of how far the distal tip is extending therefrom. Alternatively or additionally, the undercutting system may include a numeric value of the distance to which the distal tip is extending therefrom.

The undercutting system 430 generally includes a cutting assembly 432 and an undercutting guide 434, as illustrated in FIG. 18. The cutting assembly 432 may have an elongated configuration with a proximal end 440 and a distal end 442. The proximal end 440 may be located outside of the patient while the undercutting system 430 is in use.

At least a portion of the cutting assembly 432 may be formed with flexibility along a first plane and rigidity along a second plane that is oriented generally perpendicular to the first plane.

In certain embodiments, the portion of the cutting assembly 432 that is proximate to the cutting head 438 is formed from a resilient material. Forming at least a portion of the cutting assembly 432 from the resilient material enables the cutting head 438 to exert pressure against the surface of the ilium 414 and/or the sacrum 416 to remove tissue from the surfaces thereof to prepare the surfaces for fusion. This configuration also enables the cutting head 438 to be deflected in response to a shape of the region 412 between the ilium 414 and/or the sacrum 416 that is not flat and/or not transverse to the aperture even though FIG. 1 illustrates that the aperture 410 is oriented generally perpendicular to the surfaces of the ilium 414 and the sacrum 416.

A cutting head 438 may be attached to the distal end 442 of the cutting assembly 432. The cutting head 438 may take a variety of configurations, as is discussed below in more detail.

The undercutting guide 434 may have a generally cylindrical shape with a proximal end 444 and a distal end 446. The proximal end 444 may be located outside of the patient while the undercutting system 430 is in use.

The undercutting guide 434 may have a guide channel 450 that extends therethrough to facilitate guiding the cutting head 438 to a desired location in the region 412 between the ilium 414 and the sacrum 416. The guide channel 450 may have a size that is slightly larger than a size of the cutting assembly 432 to enable the cutting assembly 432 to freely move with respect to the guide channel 450. The guide channel 450 may be formed with a profile that conforms to a profile of the cutting assembly 432. For example, the guide channel 450 and the cutting assembly 432 may be formed with a circular profile.

A proximal portion 452 of the guide channel 450 proximate the proximal end 444 may be generally aligned along an axis of the undercutting guide 434. A distal portion 454 of the guide channel 450 proximate the distal end 446 may be oriented generally transverse to the axis of the undercutting guide 434. An intermediate portion 456 of the guide channel 450 may be curved to provide a transition between the proximal portion 452 and the distal portion 454.

To facilitate directing the cutting assembly 432 and the guide 434 into the aperture 410, the guide shaft 436 may be used. The guide shaft 436 may extend from the ilium 414 to a location outside of the patient's body. It is also possible to form the guide shaft 436 in shorter lengths.

The guide shaft 436 may have an inner surface that generally conforms to an outer surface of the undercutting guide 434. In certain embodiments, the guide shaft 436 and the undercutting guide 434 both have a generally circular profile. The undercutting guide 434 may have a diameter that is slightly smaller than a diameter of the guide shaft 436 so that the undercutting guide 434 may freely move with respect to the guide shaft 436.

The cutting assembly 432 is initially positioned so that an end of the cutting head 438 is positioned within the guide channel 450, as illustrated in FIG. 19. The undercutting guide 434 is moved into the shaft 436 so that the distal end 458 of the undercutting guide 434 is positioned proximate the sacrum 416, as illustrated in FIG. 20. Depending on the shape of the distal end 458, it may be necessary to remove a portion of the sacrum 416 that is adjacent to the distal end 458 so that the distal end 458 is partially recessed in the sacrum 416.

The cutting assembly 432 is then moved inwardly so that the cutting head 438 extends beyond the guide channel 450 and contacts the surfaces of the ilium 414 and/or the sacrum 416. The undercutting system 430 is rotated to cause the cutting head 438 to remove cartilage from the surface of the ilium 414 and/or the sacrum 416 to thereby prepare the ilium 414 and the sacrum 416 for fusion.

A variety of techniques may be used to rotate the undercutting system 430. In certain embodiments, the undercutting system 430 is rotated by hand. In other embodiments, a powered device or an energy storage device may be used to cause the undercutting system 430 to rotate. An example of a powered device that may be used to rotate the undercutting system 430 is a drill.

Figure 21:
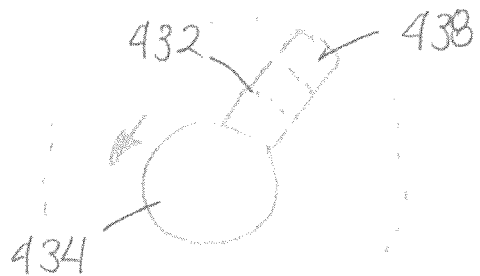
FIG. 21 is an end view of the cutting assembly of FIG. 18 when in the extended configuration.

A person of skill in the art will appreciate that this process causes a circular or partially circular region to be prepared. Depending on the area of the bone surface that must be prepared, the cutting assembly 432 may be moved with respect to the guide 434 to cause a size of the prepared region to be increased. FIG. 21 illustrates with dotted lines where the cutting head 438 has been extended several different distances from the guide 434 to prepare a successively larger area of the ilium 414 and/or the sacrum 416.

Depending on a width of the cutting head 438, it may be necessary to move the undercutting guide 434 with respect to the ilium 414 to cause the cutting head 438 to be alternately positioned proximate the surfaces of the ilium 414 and the sacrum 416.

Figure 22:
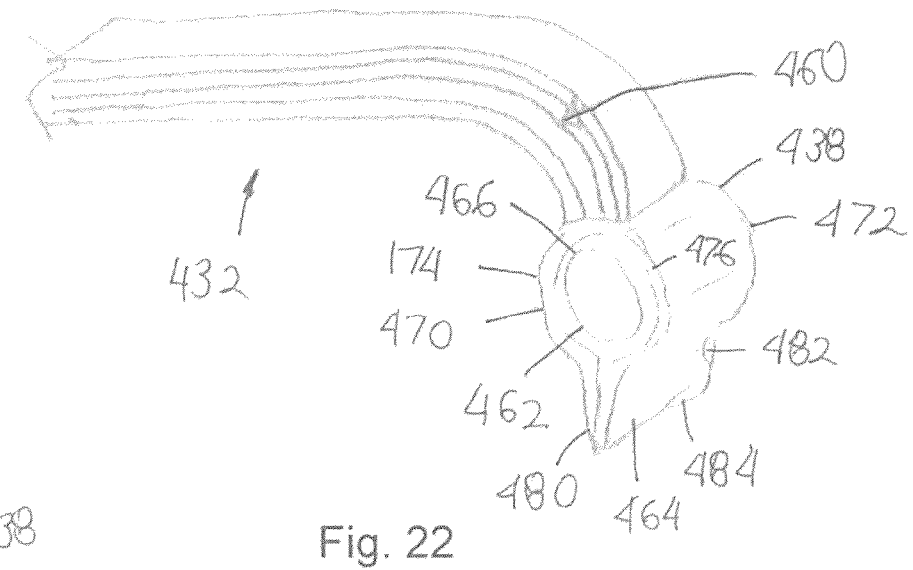
FIG. 22 is a perspective view of a cutting assembly of FIG. 18.

The cutting assembly 432 may be fabricated from a plurality of layers 460 of resilient material, as illustrated in FIG. 22. In certain embodiments, the layers 460 can be formed from nitinol. To enhance the ability of the layers to slide with respect to each other and tether broken pieces, a low friction high tensile strength material such as mylar may be placed between each of the layers 460 of resilient material.

Forming the cutting assembly 432 with this configuration enables the cutting assembly 432 to bend as the cutting assembly 432 moves through the intermediate portion 456. This configuration also provides the cutting assembly 432 with lateral strength to cut through the cartilage between the ilium 414 and the sacrum 416.

At least a portion of the cutting assembly 432 may be hollow to enable fluid to be transported into and out of the region 412. The cutting assembly 432 may include more than one fluid transmission channel such that one of the fluid transmission channels may be used for delivering a rinsing fluid and another fluid transmission channel may be used to remove the rinsing fluid and debris.

At least a portion of the outer surface of the cutting assembly 432 may be covered with a plurality of bristles. The bristles may be used to catch debris generated by the cutting head 438. The cutting assembly 432 may be periodically withdrawn from the guide 434 so that the debris can be removed from the bristles.

In one configuration, the cutting head 438 has a generally cylindrical cutting section 462 and a cutting tip 464, as illustrated in FIG. 22. The cylindrical cutting section 462 may be oriented generally transverse to an axis of the cutting assembly 432. The cylindrical cutting section 462 may have a cutting surface 466 proximate opposite ends thereof.

Forming the cylindrical cutting section 462 with the preceding configuration enables the cutting to be performed at both ends 470, 472 of the cutting assembly 432 when the cutting assembly 432 is rotated clockwise or counter clockwise. Additionally, this configuration enables cutting to be performed on both sides 474, 476 of the cutting head 438.

The cutting tip 464 extends from a distal side of the cylindrical cutting section 462. The cutting tip 464 may be a pointed configuration. The cutting tip 464 may have cutting surfaces 468 proximate both ends 480, 482 thereof as well as along a tip 484. The cutting tip 464 thereby enables the cartilage to be cut as the cutting assembly 432 is inserted further.

Figure 23:
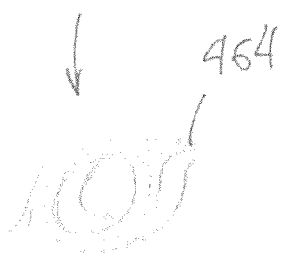
FIG. 23 is an alternative configuration of a cutting head for the undercutting system of FIG. 18.
Figure 24:
FIG. 24 is an alternative configuration of a cutting head for the undercutting system of FIG. 18.
Figure 25:
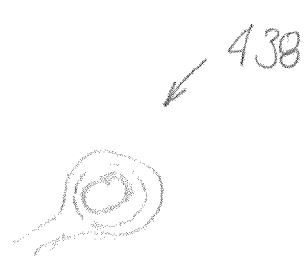
FIG. 25 is an alternative configuration of a cutting head for the undercutting system of FIG. 2.

The cutting head 438 may have a variety of configurations using the concepts of the invention. FIG. 23 illustrates an alternative configuration of the cutting head 438 in which the cutting tip 464 is shorter than the cutting tip 464 illustrated in FIG. 22. The cutting head 438 in FIG. 24 is generally in the shape of a flat-ended loop curette. The cutting head 438 in FIG. 25 is generally in the shape of a ring curette. A person of skill in the art will appreciate that a variety of surfaces of the preceding cutting head configurations may be cutting surfaces.

Figure 26:
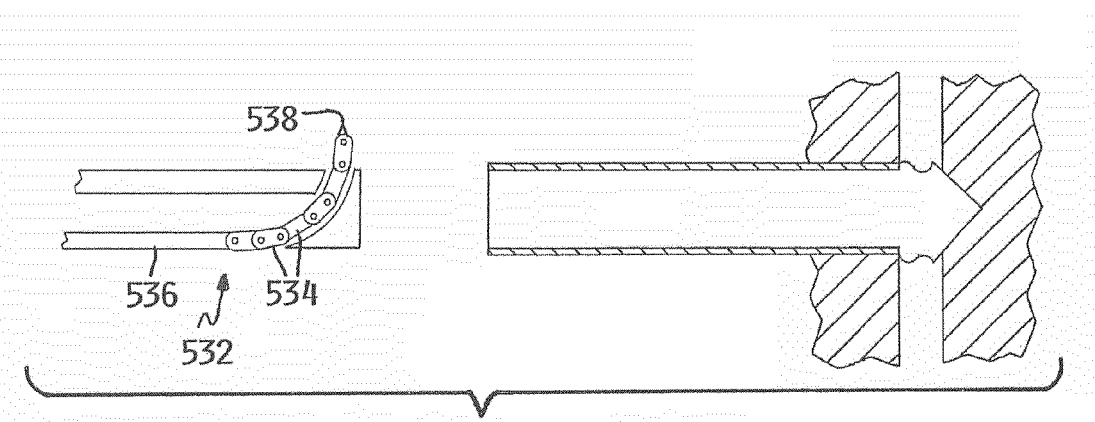
FIG. 26 is a sectional view of an alternative undercutting system positioned adjacent to an undercutting guide that has been inserted into the aperture formed in the ilium.

In another embodiment, at least a portion of the cutting assembly 532 may be formed from a plurality of links 534, as illustrated in FIG. 26. The links 534 may be attached to an operator shaft 536. The links 534 may be pivotally attached to each other. This configuration enables the cutting assembly 532 to bend such as when passing through the intermediate portion 556. The links 534 also provide the cutting assembly 532 with lateral strength so that cutting can occur when the cutting assembly 532 is rotated.

A cutting head 538 may be operably attached to a distal link 534. The mounting of the cutting head 538 to the distal link may enable the cutting head 538 to be detached from the distal link 534 such as when it is desired to use another type of cutting head 538 or when the cutting head 538 becomes dull and needs to be replaced. The cutting head 538 may have a similar configuration to the cutting heads 38 illustrated in FIGS. 22-25.

Figure 27:
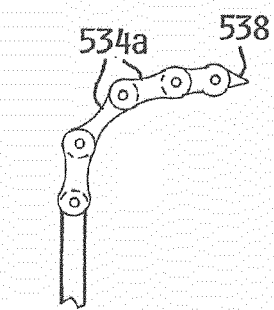
FIG. 27 is a side view of a cutting assembly for the undercutting system of FIG. 26.
Figure 28:
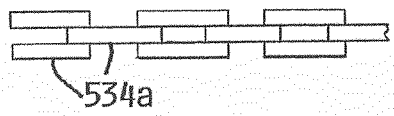
FIG. 28 is a top view of the cutting assembly of FIG. 27.
Figure 29:
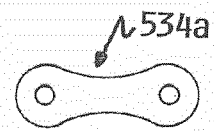
FIG. 29 is a side view of a link for the cutting assembly of FIG. 27.

The links 534 may have a variety of configurations using the concepts of the invention. One configuration of the links 534a is illustrated in FIGS. 27-29. The links 534a in this configuration are shaped similar to a conventional bicycle chain and include alternating big and small links. Opposite ends of the big links and the small links are pivotally attached to each other.

Figure 30:
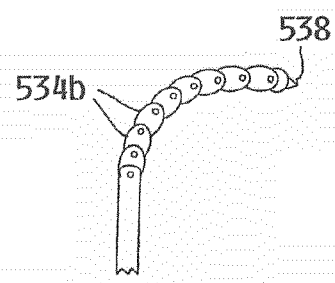
FIG. 30 is a side view of an alternative configuration of the cutting assembly for undercutting system of FIG. 28.
Figure 31:
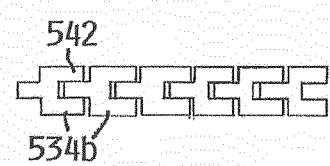
FIG. 31 is a top view of the cutting assembly of FIG. 30.
Figure 32:
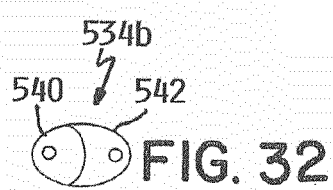
FIG. 32 is a side view of a link for the cutting assembly of FIG. 30.

An alternative configuration of the links 534b is illustrated in FIGS. 30-32. Each of the links 534b is formed substantially similar to each other. The links 534b each may have a generally oval shape with a first end 540 and a second end 542. The first end 540 may have a tab extending therefrom. The second end 542 may include a recess that is adapted to receive the tab for pivotal mounting of two adjacent links 534.

Figure 33:
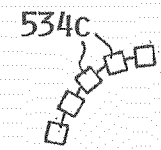
FIG. 33 is a side view of another configuration of the cutting assembly for the undercutting system of FIG. 26.
Figure 34:
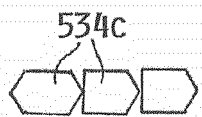
FIG. 34 is a top view of the cutting assembly of FIG. 33.
Figure 35:
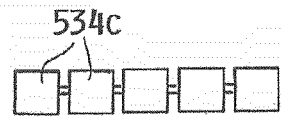
FIG. 35 is a top view of an alternative configuration of the cutting assembly of FIG. 33.
Figure 36:
FIG. 36 is a perspective view of an alternative configuration of the cutting assembly for the undercutting system of FIG. 26.

Another configuration for the links 534c is illustrated in FIGS. 33-35. The links 534c may be formed by cutting a piece of metallic or plastic material. The cuts enable the cutting assembly to be curved. The cuts may be formed to produce a plurality of blocks that each have a pointed surface at one end thereof, as illustrated in FIG. 36. Alternatively or additionally, the cuts may be formed to provide a series of blocks that are each connected with a narrow diameter section.

Yet another configuration of the cutting assembly 532 includes forming a plurality of cuts 544 in a tube, as illustrated in FIG. 36. The cut tube thereby permits bending along at least one axis. A person of skill in the art will appreciate that a variety of techniques may be used for form the cuts.

Figure 37:
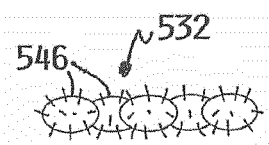
FIG. 37 is a side view of an alternative configuration of the cutting assembly for the undercutting system of FIG. 26.

Still another embodiment of the cutting assembly 532 is illustrated in FIG. 37. This embodiment includes a plurality of bristles or burrs 546 on a surface of the links. As is discussed above, the bristles or burrs 546 may be used to collect debris that is generated in the cutting process.

Figure 38:
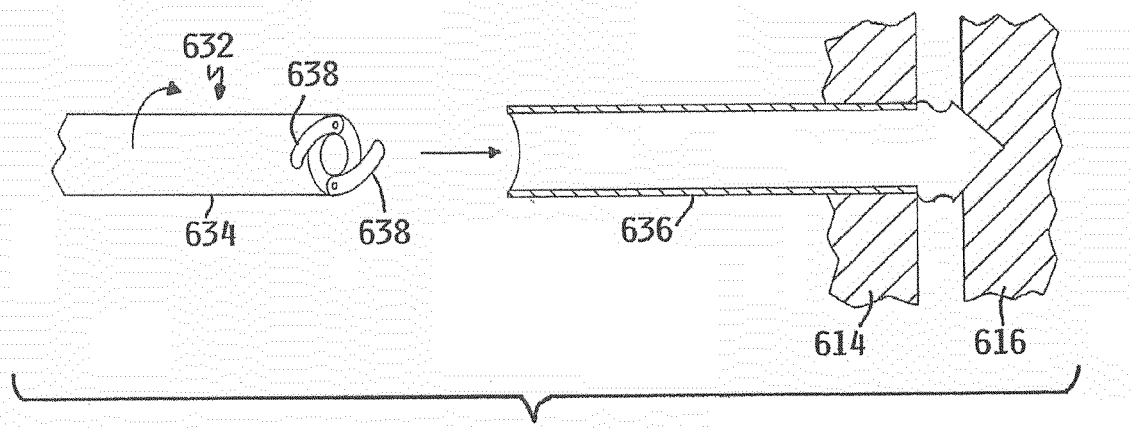
FIG. 38 is a sectional view of an alternative undercutting system positioned adjacent to an undercutting guide that has been inserted into the aperture formed in the ilium.

Another configuration of the cutting assembly 632 is illustrated in FIG. 38. The cutting assembly 632 includes an operator shaft 634 and at least one cutting head 638 operably connected to a distal end of the operator shaft 634.

In many configurations, the operator shaft 634 may be relatively rigid. In other configurations, the shaft may be flexible similar to the configuration of a speedometer cable that is used on an automobile or bicycle.

Figure 2:
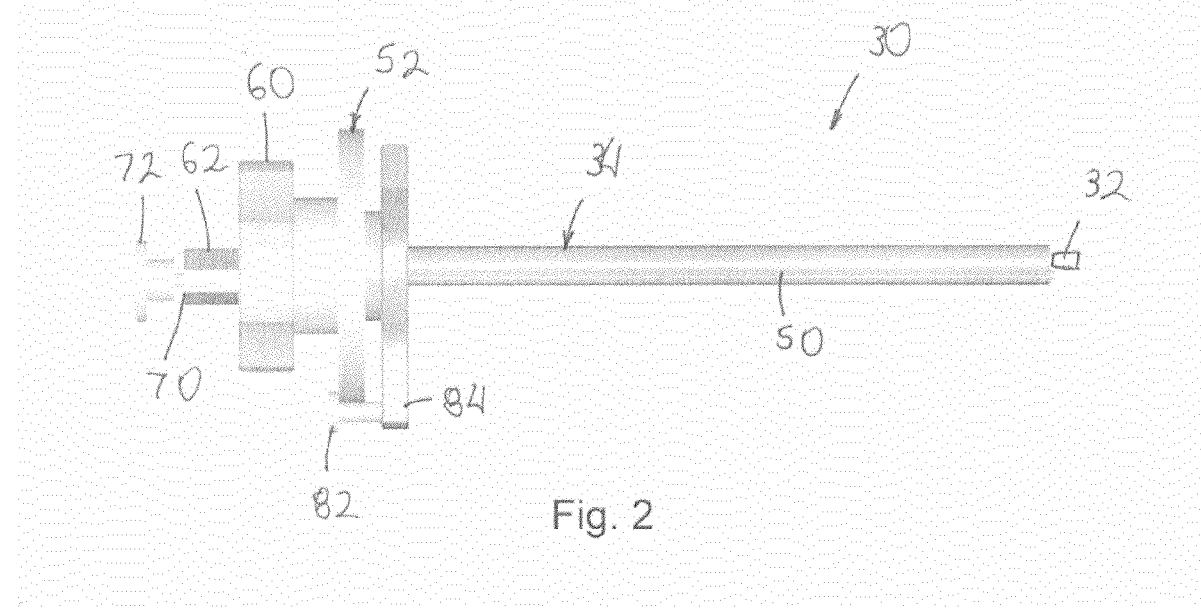
FIG. 2 is a side view of the undercutting system of FIG. 1.
Figure 4:
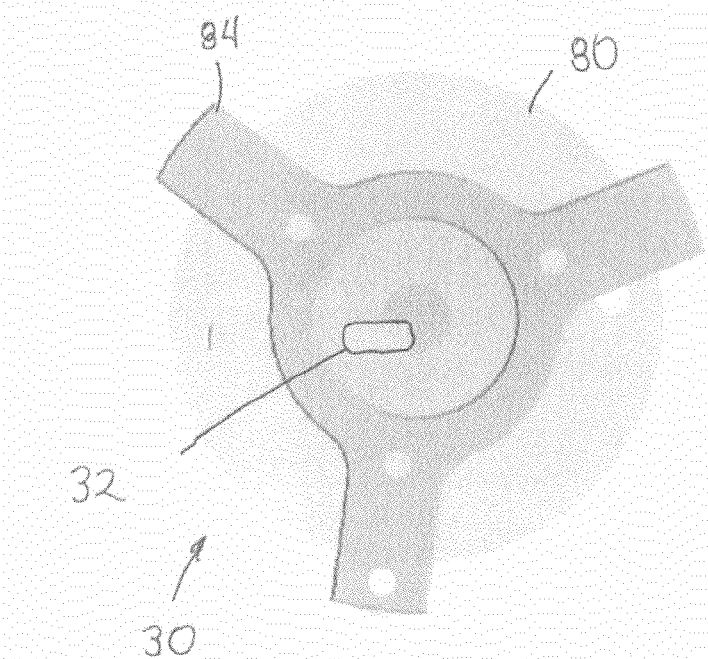
FIG. 4 is a second end view of the undercutting system of FIG. 1.
Figure 10:
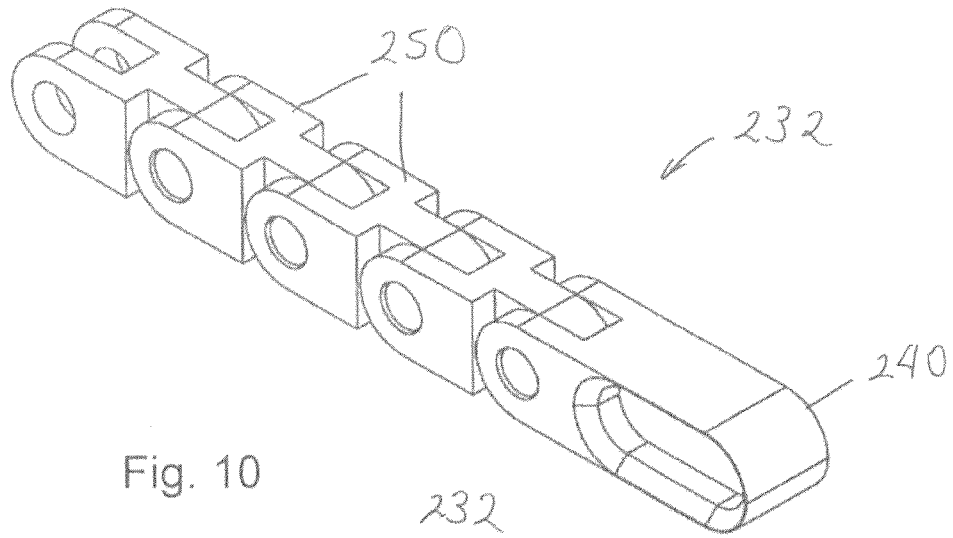
FIG. 10 is a perspective view of an end portion of a first cutting assembly for use with the undercutting system.
Figure 11:
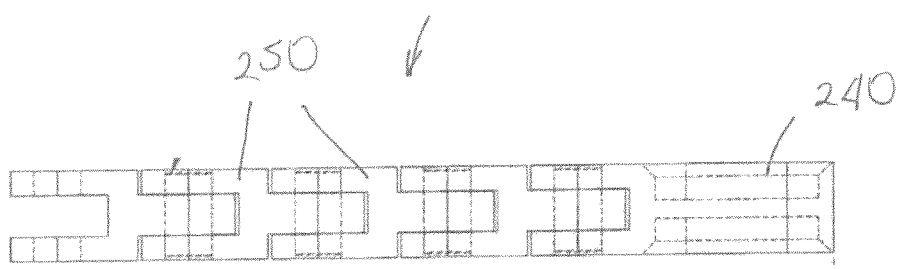
FIG. 11 is a top view of the end portion of the first cutting assembly of FIG. 10.
Figure 12:
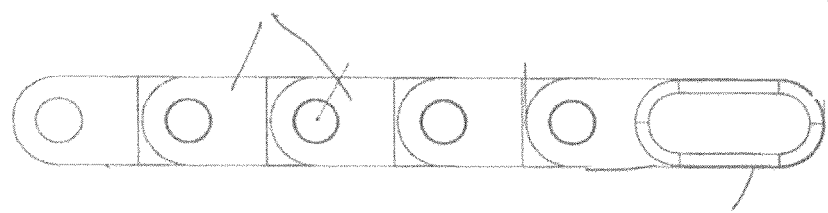
FIG. 12 is a side view of the end portion of the first cutting assembly of FIG. 10.
Figure 13:
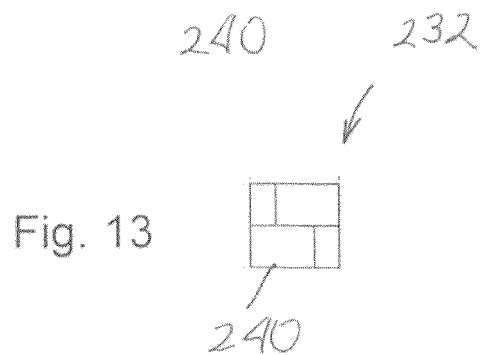
FIG. 13 is an end view of the end portion of the first cutting assembly of FIG. 10.

Similar to the undercutting guide 34 illustrated in FIGS. 2-4, the operator shaft 634 may have a shape that conforms to a shape of the guide shaft 636. In certain embodiments, the operator shaft 634 and the guide shaft 636 both have a substantially cylindrical shape. A diameter of the operator shaft 634 is slightly smaller than a diameter of the guide shaft 636. The configuration enables the cutting assembly 632 to slide with respect to the guide shaft 336.

A central portion of the operator shaft 634 may be hollow to facilitate introducing a flushing fluid and/or removing debris that has been generated from the use of the cutting assembly 632.

While the figures illustrate that the cutting assembly 632 includes two cutting heads 638, the number of cutting heads may be varied. For example, a single cutting head 638 or a larger number of cutting heads may be used.

Figures 39, 40:
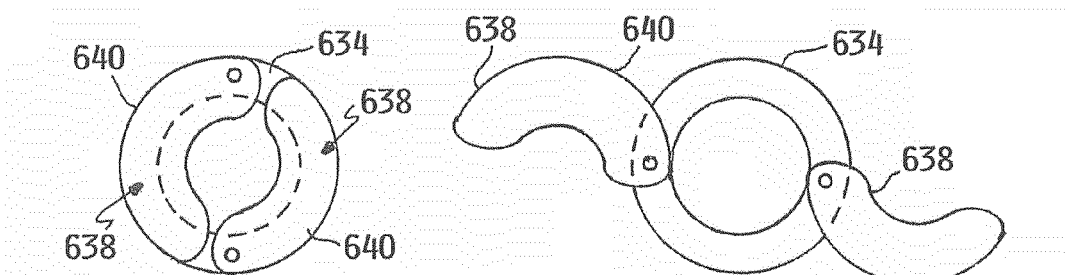
FIG. 39 is an end view of a cutting head for the undercutting system of FIG. 38 where the cutting head is in a retracted position.
FIG. 40 is an end view of the cutting head for the undercutting system of FIG. 38 where the cutting head is in an extended position.

The cutting head 638 may be positioned in a retracted position (FIG. 39) and an extended position (FIG. 40). When in the retracted position, an outer surface of the cutting head 638 is generally no wider than a width of the operator shaft 634. Using such a configuration enables the cutting assembly 632 to be moved through the guide shaft 636 without the cutting head 638 impeding such movement.

When in the extended position, the cutting head 638 extends outwardly from the operator shaft 634. A cutting surface on the cutting head 638 engages tissue between the ilium 614 and the sacrum 616 and thereby causes the tissue to be cut so that the tissue may be removed.

In certain embodiments, centrifugal force caused by rotation of the cutting assembly 632 causes the cutting head 638 to move from the retracted position to the extended position.

Rotating the cutting assembly in an opposite direction causes the cutting head 638 to move back to the retracted position. It is also possible to use mechanical mechanisms for moving the cutting head 638 between the retracted and extended configurations.

The cutting head 638 may have a variety of configurations using the concepts of the invention. In certain embodiments, the cutting head 638 has a curved configuration so that an outer surface 640 of the cutting head 638 at least partially conforms to an outer surface of the operator shaft 634.

Figures 41, 42:
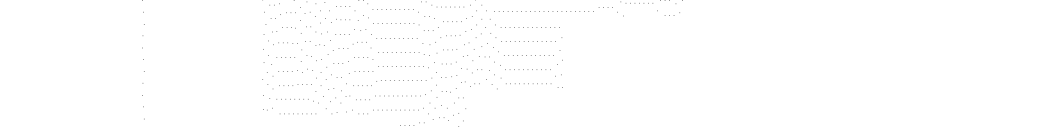
FIG. 41 is a perspective view of a cutting arm for use on the cutting head illustrated in FIGS. 39 and 40.
FIG. 42 is a perspective view of an alternative configuration of a cutting arm for use on the cutting head illustrated in FIGS. 39 and 40.

In one embodiment, the cutting head 638 includes a plurality of cutting elements 642 on the outer surface 640, as illustrated in FIG. 41. While not illustrated, the cutting elements 642 may also be provided on the upper and lower surfaces 644, 646 of the cutting head 638. As the cutting elements 642 engage tissue, the cutting elements 642 cause bits of the tissue to be cut off similar to the action of a cheese grater.

An alternative configuration of the cutting head 638 includes a plurality of burrs or bristles 650 on the outer surface 640, the upper surface 644 and the lower surface 646, as illustrated in FIG. 42. The burrs or bristles 650 may also be provided on the upper and lower surfaces of the cutting head 638. As the burrs or bristles 650 engage tissue, the burrs or bristles 650 cause bits of the tissue to be cut off. The bits of tissue may be retained in the burrs or bristles 650 to facilitate removing the bits of tissue.

Figures 43, 44:
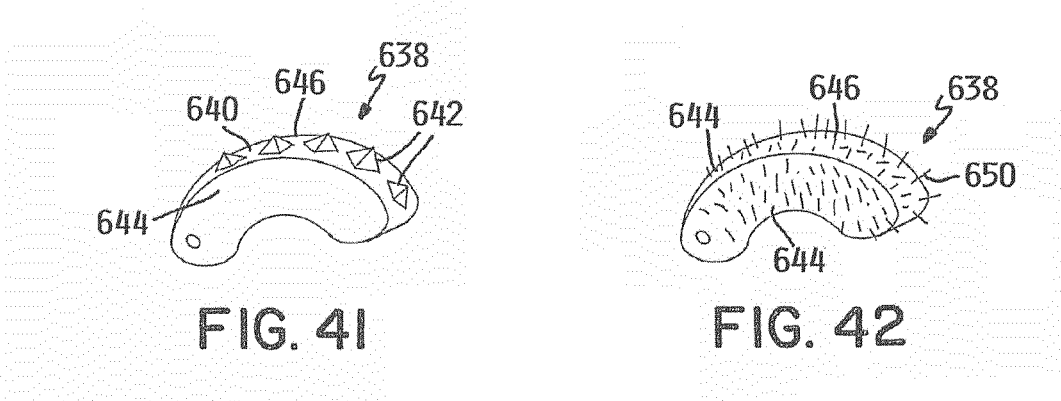
FIG. 43 is a perspective view of an alternative configuration of a cutting arm for use on the cutting head illustrated in FIGS. 39 and 40.
FIG. 44 is a perspective view of an alternative configuration of a cutting arm for use on the cutting head illustrated in FIGS. 39 and 40.

Another configuration of the cutting head 638 includes a loop curette 652 formed therein, as illustrated in FIG. 43. The loop curette 652 may be positioned proximate a distal end of the cutting head 638. While the loop curette 652 is illustrated as occupying a relatively small portion of the cutting head 638, it is possible for the loop curette 652 to occupy a larger portion of the cutting head 638.

Still another configuration of the cutting head 638 includes cutting edges 654 proximate upper and lower surfaces 644, 646 thereof, as illustrated in FIG. 44. Intermediate the cutting edges 654 may be a recessed region 652.

Figure 45:
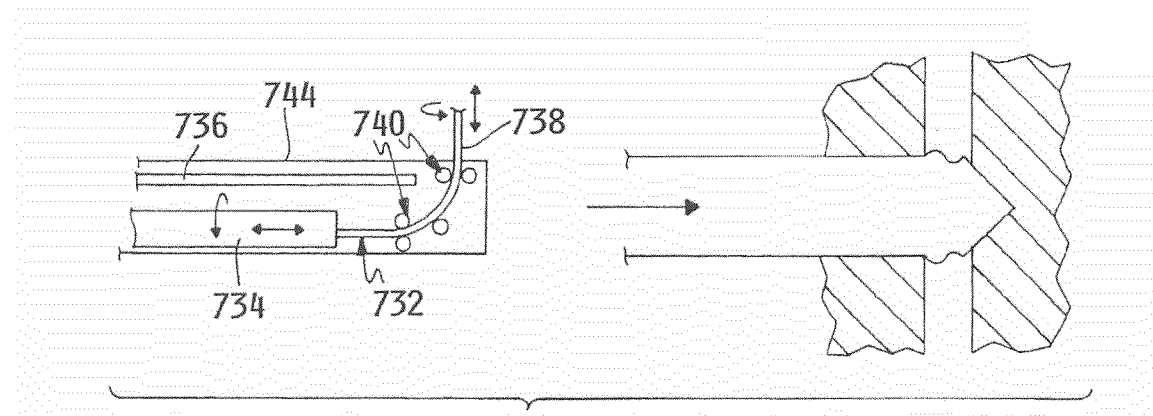
FIG. 45 is a sectional view of an alternative undercutting system positioned adjacent to an undercutting guide that has been inserted into the aperture formed in the ilium.

Another configuration of the cutting assembly 732 includes a reciprocating cutting head 736, as illustrated in FIG. 45. Alternatively or additionally, the cutting head 738 may be rotated to produce the cutting action.

The cutting assembly 732 includes an operator shaft 734 and a cutting head 738 that is operably attached to a distal end of the operator shaft 734. Depending on the anticipated operating mechanism of the cutting assembly 732, the operator shaft 734 may be reciprocally or rotationally mounted in the guide shaft 736.

The cutting head 738 may have a plurality of cutting teeth formed therein. Alternatively, the cutting head 738 may have an abrasive attached to a surface thereof having a configuration that is similar to a rasp. The cutting head 738 may be fabricated from a flexible material that enables the cutting head 738 to be curved from an orientation parallel to an axis of the cutting assembly 732 to an orientation perpendicular the axis of the cutting assembly 732, as illustrated in FIG. 45.

The guide shaft 736 may include a plurality of guide rollers 740 that facilitate changing the orientation of the cutting head 738 from parallel to the axis of the cutting assembly 732 to the orientation perpendicular the axis of the cutting assembly 732. Alternatively, a tube or a sheet of durable material may be used to guide the cutting head 738.

The guide shaft 736 may include at least one tube or channel 744 to facilitate delivering an irrigation fluid or suction that are used to remove debris generated by the cutting process.

Figure 46:
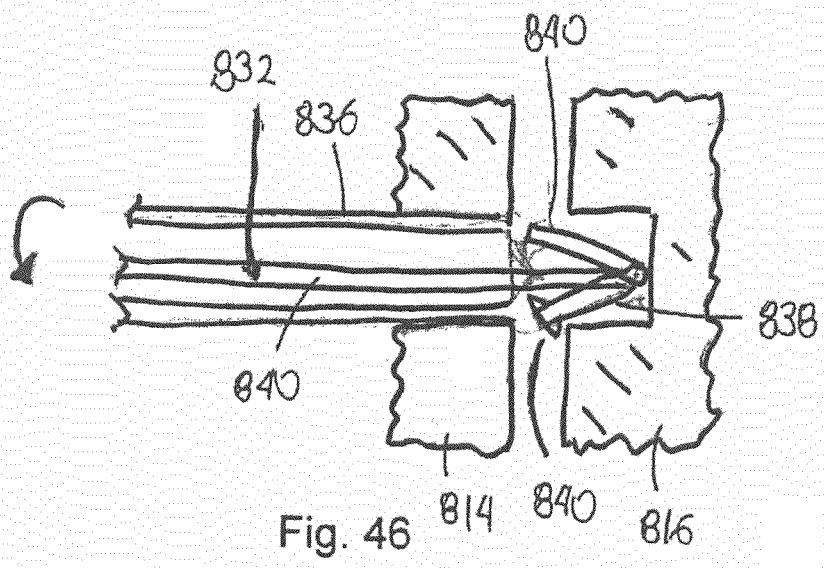
FIG. 46 is a sectional view of an alternative undercutting system inserted into the aperture formed in the ilium where a cutting head is in a retracted position.
Figure 47:
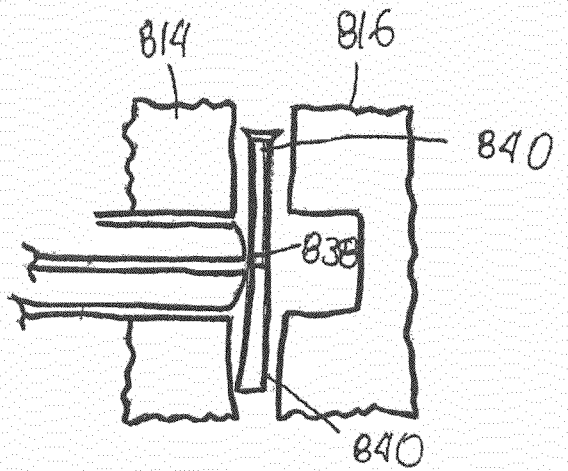
FIG. 47 is a sectional view of the undercutting system of FIG. 42 where the cutting head is in an extended position.

Another configuration of the cutting assembly 832 includes an umbrella-type mechanism, as illustrated in FIGS. 46-47. The cutting head 838 may include at least two cutting arms 840. The cutting arms 840 are initially in a retracted configuration (FIG. 46). After insertion of the cutting assembly 832, the cutting arms 840 are moved to the extended configuration (FIG. 47).

Similar to the cutting heads discussed with respect to the other configurations of the cutting assembly, the cutting arms 840 have a sharp surface on an outer surface thereof. The sharp surface may be on the upper edge, the lower edge and/or the outer edge. A variety of techniques may be used to provide the sharp surface.

The cutting arms 840 are initially in the retracted position. When in the retracted position, the outer surface of the cutting arms 840 is within a diameter of the guide tube 836. After the cutting assembly 832 is inserted into the aperture 10, the cutting arms 840 are allowed to move from the retracted position to the extended position.

The cutting arms 840 may be biased to the extended position. Once the cutting arms 840 are in the extended position, the operator shaft 834 may be rotated to cause the tissue to be removed from between the ilium 814 and the sacrum 816. Similar to the other configurations, the cutting assembly 832 may include a channel for delivering irrigation fluid or vacuum.

The cutting arms 840 may be pivotally mounted to the operator shaft 834 so that the cutting arms 840 may pivot with respect to the operator shaft 834 when in the extended position, as illustrated in FIGS. 48 and 49. Pivoting of the cutting arms 840 enables the cutting arms to conform to a surface of the ilium or the sacrum when the surface is not substantially perpendicular to the axis of the operator shaft 834.

In another configuration of the cutting assembly 932, the cutting head 938 includes a plurality of cutting arms 940 extending therefrom, as illustrated in FIG. 50. The cutting arms 940 may have a generally rectangular configuration with a cutting surface 942 along opposite edges thereof. A cutting surface 944 may also be provided on a distal edge of the cutting arms 940. The configuration of the cutting arms 940 provides the cutting arms 940 with rigidity so that the cutting arms 940 resist bending sideways in response to rotation of the cutting assembly 932 during the cutting process.

The cutting arms 940 may be formed from a flexible material so that the cutting arms may be moved between a refracted configuration (FIG. 50) and an extended configuration (FIG. 51). When the cutting arms 940 are in the retracted configuration, the cutting arms 940 are substantially within a diameter of the cutting assembly 932.

The cutting assembly 932 has a deflector mechanism 946 mounted at a distal end thereof. The deflector mechanism 942 includes a curved or angled surface that changes from an orientation generally aligned with an axis of the cutting assembly 932 to an orientation generally perpendicular to the axis of the cutting assembly 932.

A distal end of the cutting arms 940 contacts the deflector mechanism 942, as cutting head 938 is moved towards the deflector mechanism 942. The deflector mechanism 942 urges the cutting arms 940 to be deflected to the extended configuration, as illustrated in FIG. 51. When the cutting arms 940 are in the extended configuration, the cutting arms 940 may engage the tissue between the ilium 914 and the sacrum 916 to cause it to be removed therefrom to prepare for the sacroiliac fusion.

Once the cutting arms 940 are in the extended configuration, the cutting assembly 932 may be rotated to cause the cutting surfaces 942, 944 to engage the tissue between the ilium 914 and the sacrum 916. In certain situations, it may be necessary to move the cutting assembly 932 so that the cutting surfaces 942, 944 alternatively engage the surface of the ilium 914 and the sacrum 916.

Once the cutting process is completed, the cutting assembly 932 is moved towards a proximal end. This movement causes the cutting arms 940 to move from the extended configuration to the retracted configuration so that the cutting assembly 932 may be withdrawn.

An alternative configuration of the cutting assembly 932 has cutting arms 940 that are tapered, as illustrated in FIG. 52. In this configuration, the cutting arms 940 have a greater width proximate a proximal end thereof than proximate a distal end thereof. Cutting surfaces 946 may be provided on the sides of the cutting arms 940.

Figure 53:
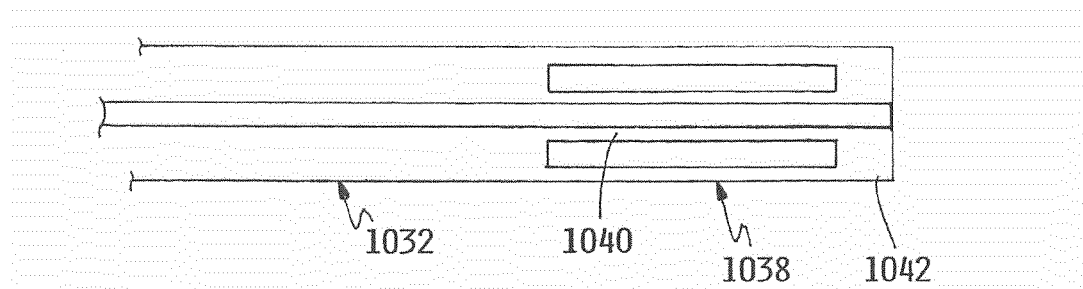
FIG. 53 is a side view of an alternative configuration of the undercutting system where the undercutting system is in a refracted configuration.

In another configuration, a distal end of the cutting assembly 1032 has a generally cylindrical configuration, as illustrated in FIG. 53. The cutting assembly 1032 has a plurality of slits 1038 formed therein to define the cutting arms 1040. The slits 1038 do not extend all the way to the distal end of the cutting assembly 1032 but rather end a distance from the distal end of the cutting assembly 1032 to define an end portion 1042.

The surfaces of the cutting assembly 1032 are cutting surfaces. A variety of techniques may be used for fabricating the cutting surfaces. Examples of the cutting surfaces include sharpened, a roughened texture or burrs attached to a surface thereof.

The cutting assembly 1032 is initially in a retracted position. When the cutting assembly 1032 is in the retracted position, an outer surface of the cutting assembly 1032 may be substantially straight, as illustrated in FIG. 53.

As the cutting assembly 1032 is inserted into the aperture 1010, the end portion 1042 engages the sacrum 1016. In certain embodiments, a recess 1044 may be formed in the sacrum 1016 that is configured to receive at least partially receive the end portion 1042.

Figure 54:
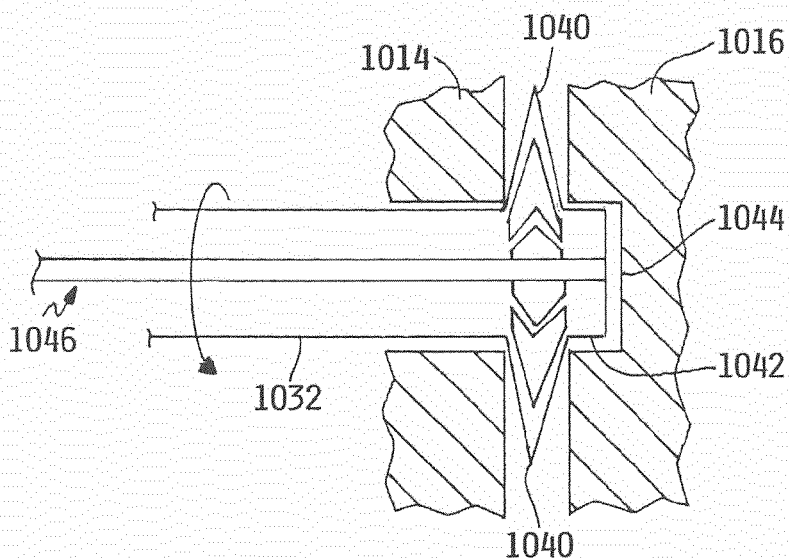
FIG. 54 is a side view of the undercutting system of FIG. 53 that has been inserted into an aperture formed in the ilium where the undercutting system is in an extended configuration.

When the cutting assembly 1032 continues to move towards the sacrum 1016, the cutting arms 1040 are deflected outwardly, as illustrated in FIG. 54, until the cutting arms 1040 are in the extended configuration. When the cutting arms 1040 are in the extended configuration, the cutting assembly 1032 may be rotated to cause tissue between the ilium 1014 and the sacrum 1016 to be removed.

The length of the slits 1038 determines how far the cutting arms 1040 outwardly extend when in the extended position. In certain embodiments, it may be necessary to use several different cutting assemblies with progressively longer slits 1038 to enable a progressively larger surface area between the ilium 1014 and the sacrum 1016 to be prepared.

Alternatively or additionally, a central shaft 1046 may be provided in the cutting assembly 1032. The central shaft 1046 may be operably connected to the end portion 1042. Holding the central shaft 1046 as the other portions of the cutting assembly 1032 are moved toward the distal end thereof may be used to urge the cutting arms 1040 from the retracted position to the extended configuration. Such a process enables the cutting arms 1040 to be moved to the extended position without placing any forces on the sacrum 1016.

Figure 55:
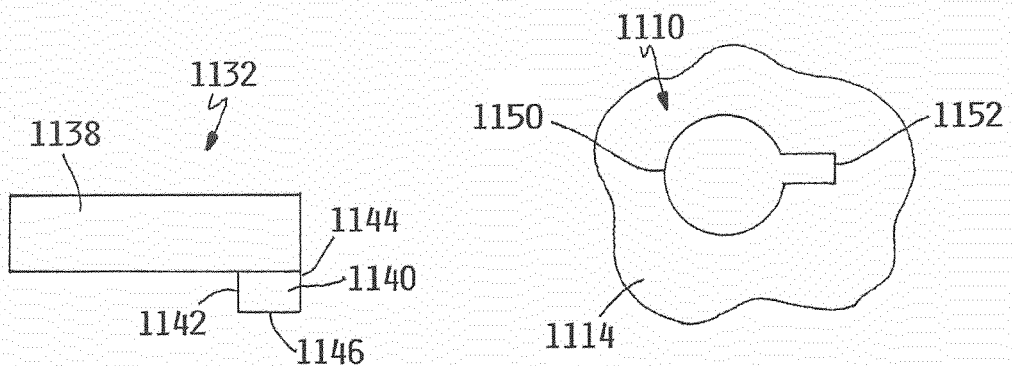
FIG. 55 is a side view of an alternative configuration of the undercutting system.

In another configuration of the cutting assembly 1132, the cutting assembly 1132 may include a central shaft 1138 and a cutting head 1140 that extends from a distal end thereof, as illustrated in FIG. 55. In this configuration, a size of the cutting assembly 1132 is greater proximate where the cutting head 1140 extends therefrom.

The cutting head 1140 may have sharp surfaces on upper and lower surfaces 1142, 1144 thereof to facilitate removing tissue from surface of the ilium 1114 and the sacrum 1116. The cutting head 1140 may also have a sharp surface on an end 1146 thereof.

A height of the cutting head 1140 may be less than a distance between the ilium 1114 and the sacrum 1116. In such a configuration, the central shaft 1138 may be moved inward or outward so that the cutting surfaces alternatively engage the ilium and the sacrum.

Figure 56:
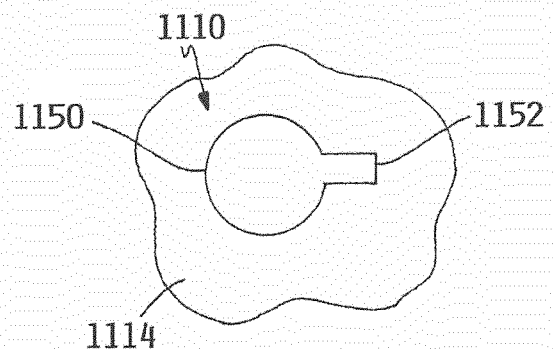
FIG. 56 is a top view of the aperture in the ilium for use with the undercutting system of FIG. 55.

The aperture 1110 formed in the ilium 1114 may have a shape that generally conforms to a shape of the cutting assembly 1132, as illustrated in FIG. 56. In certain embodiments, the aperture 1110 may be formed in two parts.

The first aperture part 1150 may have a generally circular configuration, such as may be formed by a conventional drill. The second aperture part 1152 may be generally rectangular with sides that are substantially parallel to each other. The second aperture part 1152 may be formed using a variety of techniques. An example of one such suitable technique is a reciprocating saw.

It is also possible to form the second aperture part 1152 having other configurations. The only important criterion is that the second aperture part has a length and a width that are larger than a length and a width of the cutting head 1140. An example of one other suitable technique is forming the second aperture part 1152 using a drill.

The drill bit used to form the second aperture part 1152 may have a smaller size than the drill bit used to form the first aperture part 1150. The drill bit used to form the second aperture part 1152 may be laterally offset from the position of the drill bit used to form the first aperture part 1150 so that the first aperture part 1150 and the second aperture part 1152 intersect.

Figure 57:
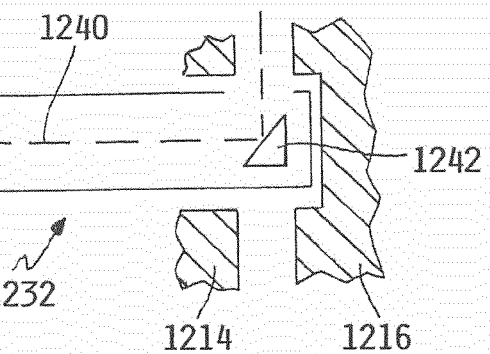
FIG. 57 is a sectional view of an alternative configuration of the undercutting system.

Another configuration of the cutting assembly 1232 uses a laser beam 1240 for removing tissue from between the ilium 1214 and the sacrum 1216, as illustrated in FIG. 57. The cutting assembly 1232 may be rotational to facilitate removing tissue in all directions around the aperture 1210.

The cutting assembly 1232 may include a reflective device 1242 to direct the laser beam 1240 between from an orientation generally aligned with an axis of the cutting assembly 1232 to an orientation generally perpendicular to the axis of the cutting assembly 1232. A person of skill in the art will appreciate that the reflective device 1242 may take a variety of configurations depending on the type of laser beam 1240 used with the cutting assembly 1232.

It may be necessary to move the cutting assembly 1232 inward and outward to enable tissue to be removed from between the surfaces of the ilium 1214 and the sacrum 1216. Alternatively or additionally, the reflective device 1242 may be movably mounted in the cutting assembly 1232 to control the direction of the laser beam.

An example of one suitable laser that may be used in conjunction with this embodiment of the cutting assembly 1232 is an excimer laser. A person of skill in the art will appreciate that other apparatuses that emit an energy beam that is capable of removing the tissue between the ilium 1214 and the sacrum 1216 in a controlled manner may also be used.

Another embodiment of the invention relates to the use of chemicals, examples of which include acids and enzymes to dissolve and/or remove tissue from between the ilium and the sacrum to thereby prepare for fusion of the sacroiliac joint may also be used. A variety of techniques may be used for supplying the chemicals and thereafter removing the chemicals and the dissolved tissue.

A fluid jet technology may be used to remove the tissue from between the ilium and the sacrum to prepare for fusion of the sacroiliac joint. Examples of the fluid jet technology that may be used include hydrocision.

A particle stream may be used to prepare the surfaces of the ilium and the sacrum for fusion of the sacroiliac joint may be used. One such stream of particle is a sand blaster. The particles may have a surface that is rough or abrasive so facilitate abrading or otherwise removing the tissue from between the ilium and the sacrum.

The particles used should be biocompatible or bioresorbable to minimize the potential of side effects on the patient if the particles are not all removed from the patient once the surfaces of the ilium and the sacrum are prepared.

The particle stream may be used in conjunction with at least two holes that are formed in the ilium and/or the sacrum. One of the holes may be used for introducing the particles into the region between the ilium and the sacrum. A separate hole may be used for collecting the particles and the tissue removed.

As an alternative or in addition to the sharp surfaces describe in the various embodiments discussed herein, the surfaces could be rough and/or abrasive to facilitate removing the tissue between the ilium and the sacrum using abrasion, as opposed to cutting.

The abrasive action may be provided by particles attached to the surface of the cutting assembly. Alternatively or additionally, the abrasive action may be provided by wires or other materials that extend from the surface of the cutting assembly.

Figure 58:
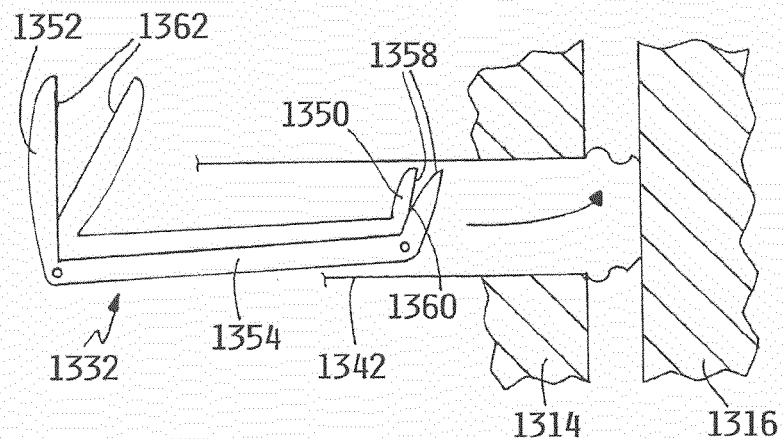
FIG. 58 is a sectional view of an alternative configuration of the undercutting system.

Another embodiment of the cutting assembly 1332 is directed to articulating rongeurs 1340 that may be used in conjunction with a docking cannular 1342, as illustrated in FIG. 58. The articulating rongeurs 1340 may generally include a cutting mechanism 1350, a control mechanism 1352 and an elongated section 1354 that interconnects the cutting mechanism 1350 and the control mechanism 1352.

The cutting mechanism 1350 may operate in a variety of manners. In one configuration, the cutting mechanism 1350 includes two jaws 1358 that are pivotally mounted to each other for movement between an open configuration and a closed configuration.

At least one of the jaws 1358 may have a cutting surface 1360. As the jaws 1358 are moved to the closed configuration, the cutting surface 1360 engages the tissue and thereby cuts away the tissue. The process is repeated until a desired amount of tissue is removed from between the ilium 1314 and the sacrum 1316.

At least one of the jaws 1358 may include a tapered end to facilitate moving the jaw 1358 between the tissue and the ilium or the sacrum to thereby enhance the ability to prepare the surfaces of the ilium and the sacrum for the sacroiliac fusion.

A length of the cutting mechanism 1350 may be less than an inner diameter of the docking cannula 1342 to facilitate passing the cutting mechanism 1350 through the docking cannula 1342.

The control mechanism 1352 facilitates operation of the cutting mechanism 1350 from a position outside of the space between the ilium 1314 and the sacrum 1316. In certain embodiments, the control mechanism 1352 may be designed for positioning outside of the patient's body when used.

The control mechanism 1352 is operably connected to the cutting mechanism 1350. In certain embodiments, there is a mechanical connection between the control mechanism 1352 and the cutting mechanism 1350. For example, the control mechanism 1352 may include two handles 1362 that are pivotally mounted to each other. Pivoting of the handles 1362 towards each other causes the jaws to pivot to each other. The handles 1362 may be biased apart from each other so that the jaws are initially in the open configuration.

Alternatively, there may be an electrical connection between the control mechanism 1352 and the cutting mechanism 1350. In such a configuration, the control mechanism 1352 may include a switch or other mechanism for causing the cutting mechanism 1350 to be activated. A mechanism may be provided on the cutting mechanism 1350 to receive the signal from the control mechanism 1352 and thereby activate the cutting mechanism 1350.

A person of skill in the art will appreciate that other mechanisms may be used for operably connecting the control mechanism 1352 and the cutting mechanism 1350. Examples of such suitable alternative mechanisms include pneumatic, vacuum and hydraulic.

The elongated section 1354 operable connects the cutting mechanism 1350 and the control mechanism 1354. The elongated section 1354 may be formed with a length that provides a desired distance between the cutting mechanism 1350 and the control mechanism 1354. In certain embodiments, the elongated section 1354 has a length of between about 2 inches and 18 inches.

While the elongated section 1354 is illustrated as being substantially straight, it is possible for the elongated section 1354 to have a variety of other configurations that enable the cutting mechanism 1350 to be operated between the ilium 1214 and the sacrum 1316 while enabling the control mechanism 1352 to be operated from a convenient position outside of the patient. The elongated section 1354 may be rigid or flexible using the concepts of the invention.

Figure 59:
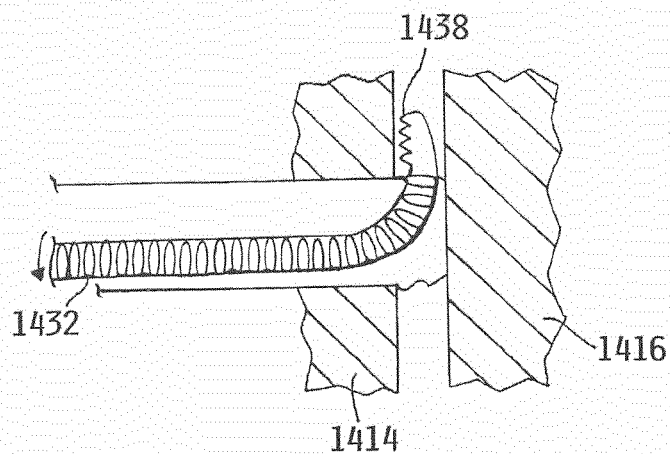
FIG. 59 is a sectional view of an alternative configuration of the undercutting system.

Yet another configuration of the cutting assembly 1432 involves forming the cutting assembly 1432 as an endius-type shaver, which is used in conjunction with a cannula, as illustrated in FIG. 59.

The endius-type shaver includes a cutting head 1438 attached to a distal end thereof. The cutting head 1438 may include a plurality of teeth and/or an abrasive. Rotation of a shaft within the cutting assembly 1432 causes the cutting head 1438 to engage the tissue between the ilium 1414 and the sacrum 1416 and thereby cut the tissue to prepare for fusion of the sacroiliac joint.

Figure 60:
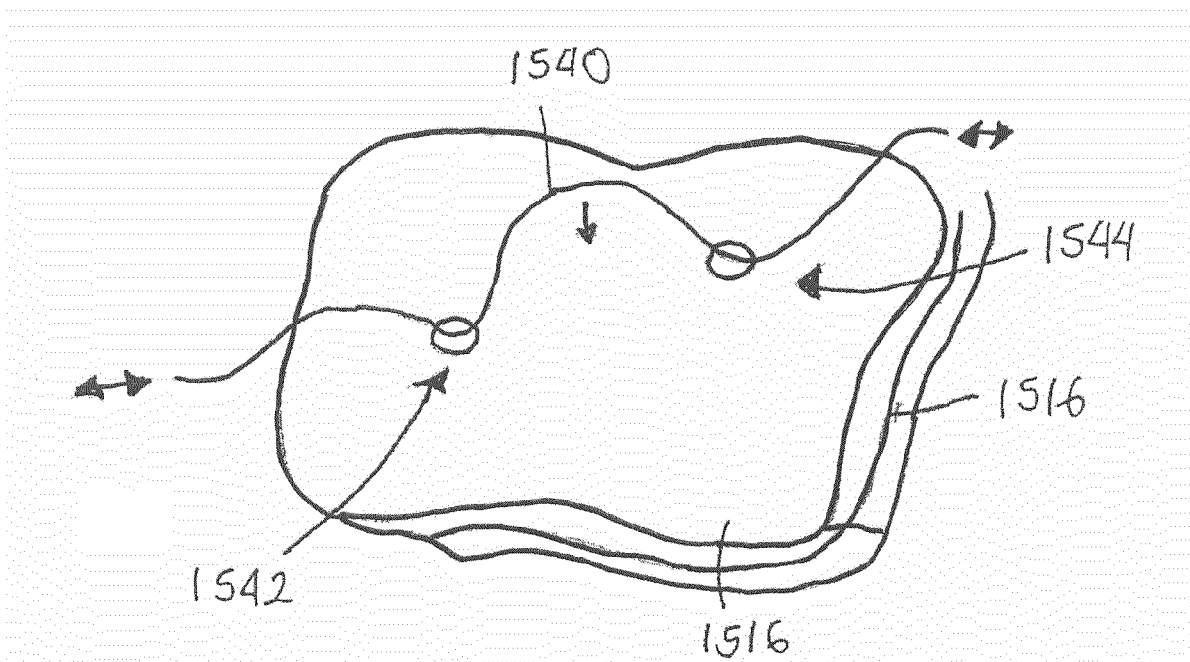
FIG. 60 is a top view of an alternative configuration of the undercutting system.

Another configuration used for preparing the surfaces of the ilium 1514 and the sacrum 1516 for fusion includes passing a line 1540 having an abrasive surface through two apertures 1542, 1544 in the ilium 1514, as illustrated in FIG. 60. As the line 1540 is moved in an oscillating motion, the abrasive causes tissue to be removed from the surfaces of the ilium 1514 and the sacrum 1516 to thereby prepare the surfaces for the fusion of the sacroiliac joint. Periodically, the separated tissue may be removed from between the ilium 1514 and the sacrum 1516. A person of skill in the art will appreciate that a variety of techniques may be used.

While FIG. 60 illustrates that two apertures 1542, 1544 are used in conjunction with the process, it is possible to use additional apertures to prepare a larger surface area for the fusion of the sacroiliac joint.

Figure 61:
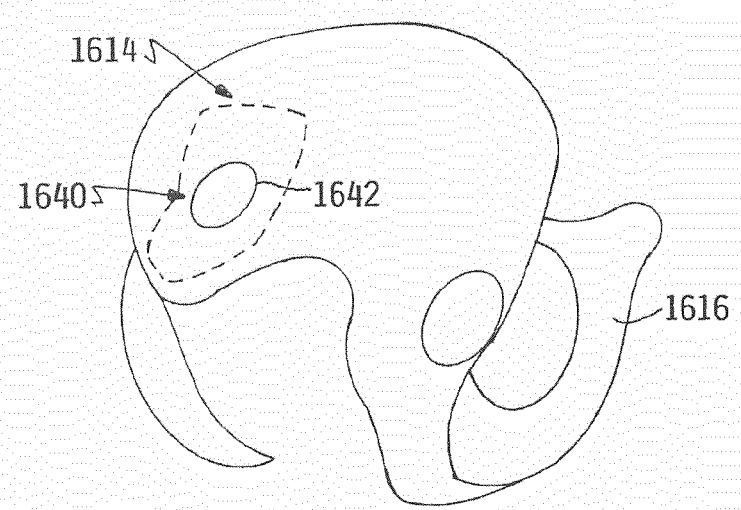
FIG. 61 is a top view of an alternative configuration of the undercutting system.

Another configuration that may be used to prepare the sacroiliac joint for fusion involves forming at least one aperture 1640 in the ilium 1614 using a device such as a hole saw that enables a substantially solid piece 1642 to be remove from the ilium 1614, as illustrated in FIG. 61.

Once the piece 1642 is removed, tissue is removed from the inner surface of the removed piece 1642 to prepare the inner surface of the removed piece 1642 for fusion. A surface of the sacrum 1616 below the removed piece is also prepared by removing tissue from the surface thereof to prepare the inner surface of the sacrum 1616 for fusion.

Thereafter, the removed piece 1642 is replaced. A variety of techniques may be used to maintain the piece 1642 in a stationary position with respect to the ilium 1614 so that bone may grow between the prepared surfaces to cause fusion of the sacroiliac joint.

Each of the apertures 1640 may have a size of up to about 1 inch. In certain embodiments, the apertures 1640 each have a diameter of between about ½ and ¾ of an inch. The number of apertures 1640 formed in the ilium may be selected to provide adequate prepared surface area on the ilium 1614 and the sacrum 1616 for fusion. There may be up to about 10 apertures 1640. In certain embodiments, there are between two and three apertures 1640.

While this configuration for preparing the surfaces of the ilium 1614 and the sacrum 1616 for the fusion of the sacroiliac joint is more invasive than many of the other techniques described herein, it is considerably less invasive than the prior art techniques for fusion of the sacroiliac joint.

Figure 62:
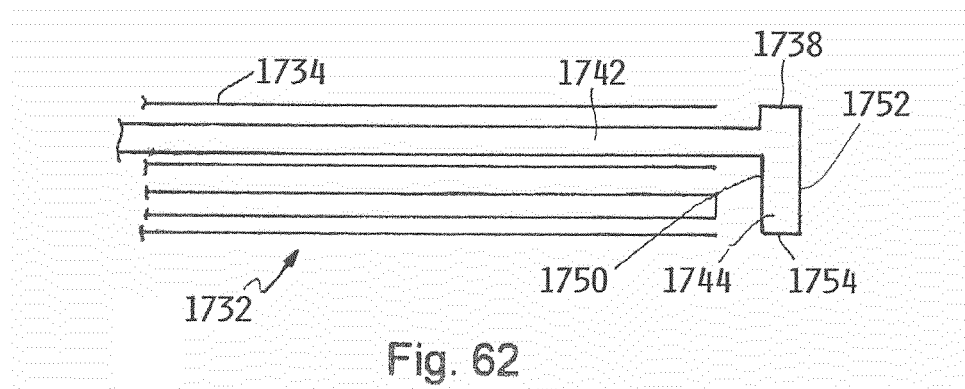
FIG. 62 is a sectional view of an alternative configuration of the undercutting system.

Another configuration of the cutting assembly 1732 is illustrated in FIG. 62. The cutting assembly 1732 may be used in conjunction with a cannula that is positioned in the aperture formed in the ilium. The cutting assembly 1732 includes an undercutting guide 1734 and a cutting head 1738.

The cutting head 1738 includes an elongated shaft 1742 and a cutting extension 1744. The cutting extension 1744 extends from one side of the elongated shaft 1742. Upper and lower surfaces 1750, 1752 of the cutting extension 1744 may have a sharpened or abrasive surface to facilitate removing material from between the ilium and the sacrum. An end surface 1754 of the cutting head 1738 may also have a sharpened or abrasive surface.

The cutting extension 1744 is mounted in an offset configuration in the undercutting guide 1734, as illustrated in FIG. 62. Mounting the cutting extension 1744 in such a manner enables the cutting extension 1744 to be moved between a refracted configuration (FIG. 62) and an extended configuration (FIG. 63).

When the cutting extension 1744 is in the refracted configuration, the cutting extension 1744 is substantially within a diameter of the undercutting guide 1734 to facilitate inserting and removing the cutting assembly 1732. When the cutting extension 1744 is in the extended configuration, the cutting extension 1744 extends beyond the undercutting guide 1734 so that the cutting extension 1744 may be used to remove tissue from between the ilium and the sacrum.

Figure 63:
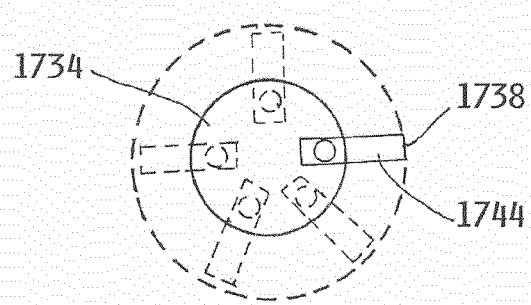
FIG. 63 is an end view of the undercutting system of FIG. 62.

The cutting extension 1744 may be maintained in a stationary position with respect to the undercutting guide 1734 and then the cutting assembly 1732 may be rotated, as illustrated by the dashed lines in FIG. 63. Depending on the thickness of the cutting extension 1744, it may be necessary to move the cutting assembly 1732 inward or outward to clear the surfaces of the ilium and the sacrum.

Multiple cutting head 1738 having cutting extensions 1744 of different lengths may be used in conjunction with the cutting assembly 1732 to thereby enable progressively larger surface areas on the ilium and the sacrum to be prepared for the sacroiliac fusion.

Figure 64:
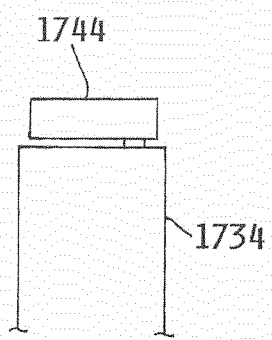
FIG. 64 is a side view of an alternative configuration of the undercutting system in a refracted configuration.

Alternatively or additionally, the cutting extension 1744 may be formed with a telescoping configuration, as illustrated in FIGS. 60 and 61. The cutting extension 1744 may be in an initial position where the cutting extension 1744 is substantially within a diameter of the undercutting guide 1734, as illustrated in FIG. 64.

Figure 65:
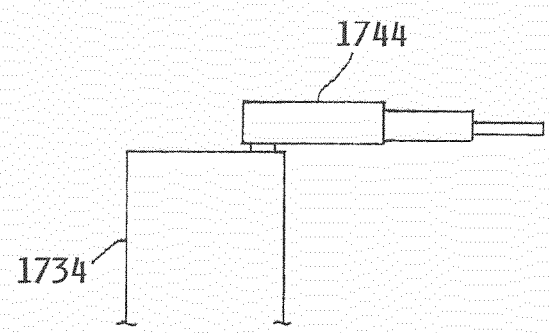
FIG. 65 is a side view of the undercutting system of FIG. 63 in an extended configuration.

The cutting head 1738 may be moved to the extended configuration, as illustrated in FIG. 65, where a length of the cutting extension 1744 is increased to increase the area of the ilium and the sacrum that may be prepared for the sacroiliac fusion.

The number of sections in the cutting extension 1744 may be selected based upon the surface area that must be prepared for the sacroiliac fusion. A variety of techniques may be used for moving the sections of the cutting extension 1744 between the retracted and extended configurations. An example of one such suitable technique is hydraulics.

Another embodiment of the cutting assembly 1832 includes a rotatable cutting head 1838, as illustrated in FIG. 66. The cutting head 1838 is mounted to a distal end of a support shaft 1834.

The cutting head 1838 has a generally circular shape and includes a cutting element 1842 on an outer surface thereof. The cutting elements 1842 may take a variety of configurations. One suitable configuration for the cutting elements 1842 is a flexible material that is adjacent to the surface of the cutting head 1838 when the cutting head 1838 is not rotated. Rotation of the cutting head 1838 may cause the cutting elements 1842 to extend outwardly.

To increase an area that is prepared with the cutting assembly 1832, the cutting head 1838 may be rotatable about an axis 1850 that is offset from a central axis of the support shaft 1834, as illustrated in FIGS. 67-69. A series of cutting heads 1838 with progressively offset axes 1850 may be used to progressively increase the area that is prepared by moving the rotational axis 1844 closer to an edge of the cutting head 1838, as illustrated by the difference between FIGS. 68 and 69.

Another configuration of the cutting assembly 1932 is illustrated in FIGS. 70 and 71. The cutting assembly 1932 may include an undercutting guide 1934 in which a cutting head 1938 is mounted.

The cutting head 1938 may include a base portion 1940 and a cutting portion 1942 that extends from a distal end of the base portion 1940 in an orientation that is generally perpendicular to the orientation of the base portion 1940. A distal end of the base portion 1940 may be angled to facilitate urging the cutting head 1938 from a refracted configuration (FIG. 70) to an extended configuration (FIG. 71). The cutting head 1938 may be biased to the retracted configuration.

The cutting portion 1942 may include a cutting surface on the upper and lower edges 1950, 1952 thereof. The cutting portion 1942 may also have a cutting surface on an outer edge 1954 thereof. The cutting surface may take a variety of configurations such as is discussed above with respect to the other configurations of the cutting assembly.

The cutting assembly 1932 may also include a biasing element 1944 with an angled distal surface 1646. When the biasing element 1944 is urged toward the distal end of the cutting assembly 1932, the angled distal surface 1846 engages the distal end of the base portion 1940 to cause the cutting head 1938 to move from the retracted configuration to the extended configuration. While it is not necessary for the angle of orientation of the two angled surfaces to be the same, the angled surfaces should be generally oriented in the same direction.

Once the cutting head 1938 is in the extended configuration, the cutting assembly 1932 may be rotated to remove tissue from between the ilium and the sacrum. After the tissue is removed, the biasing element 1944 may be moved toward the proximal end of the cutting assembly 1932. Such movement allows the cutting head 1938 to move from the extended configuration to the retracted configuration. Thereafter, the cutting assembly 1932 may be removed.

Figure 72:
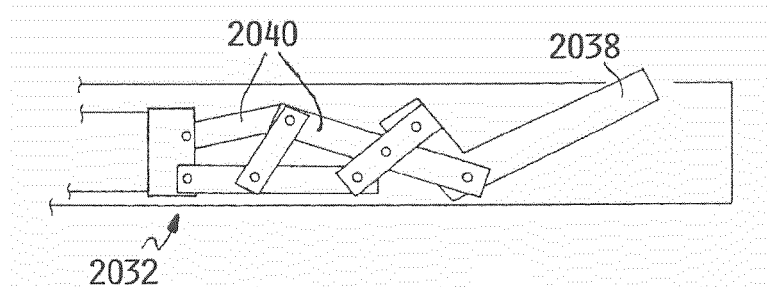
FIG. 72 is a sectional view of an alternative configuration of the undercutting system where the undercutting system is in a retracted configuration.
Figure 73:
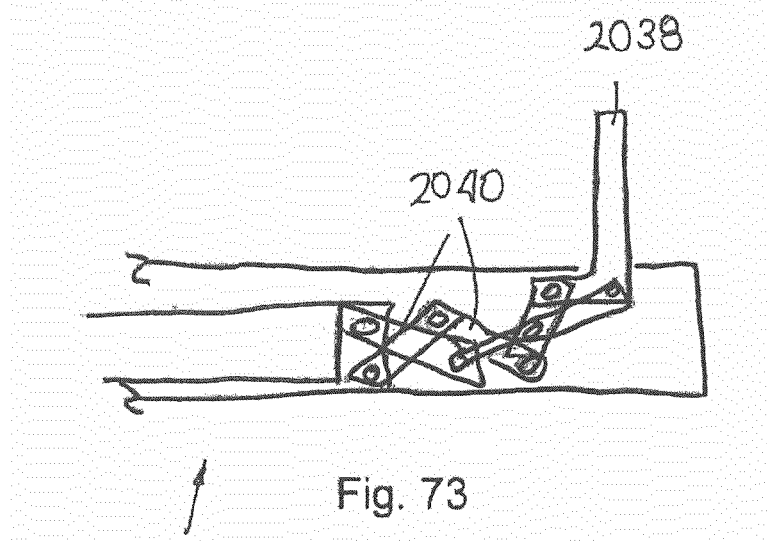
FIG. 73 is a sectional view of the undercutting system of FIG. 72 where the undercutting system is in an extended configuration.

Another configuration of the cutting assembly 2032 includes a linkage assembly having a plurality of arm sections 2040 that are pivotally mounted with respect to each other, as illustrated in FIGS. 72 and 73. The cutting assembly 2032 is mounted within an undercutting guide 2034.

The linkage assembly causes the cutting head 2038 to pivot from a retracted configuration (FIG. 72) to an extended configuration (FIG. 73). Similar to the other configurations of the cutting assembly, the cutting head 2038 may include cutting surfaces on the upper, lower and end edges thereof.

Figure 74:
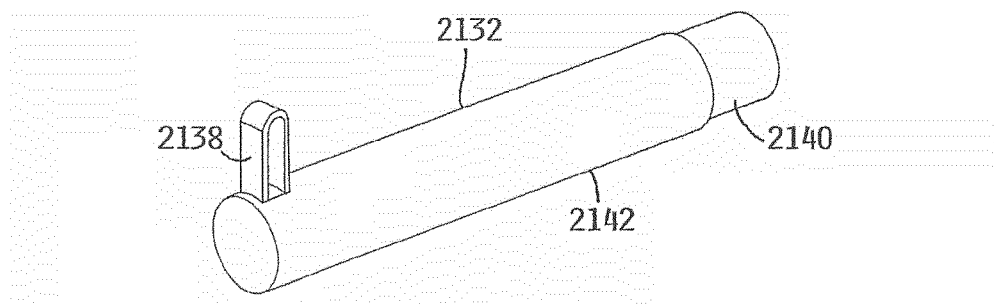
FIG. 74 is a perspective view of an alternative configuration of the undercutting system where a cutting assembly is in an extended configuration.
Figure 75:
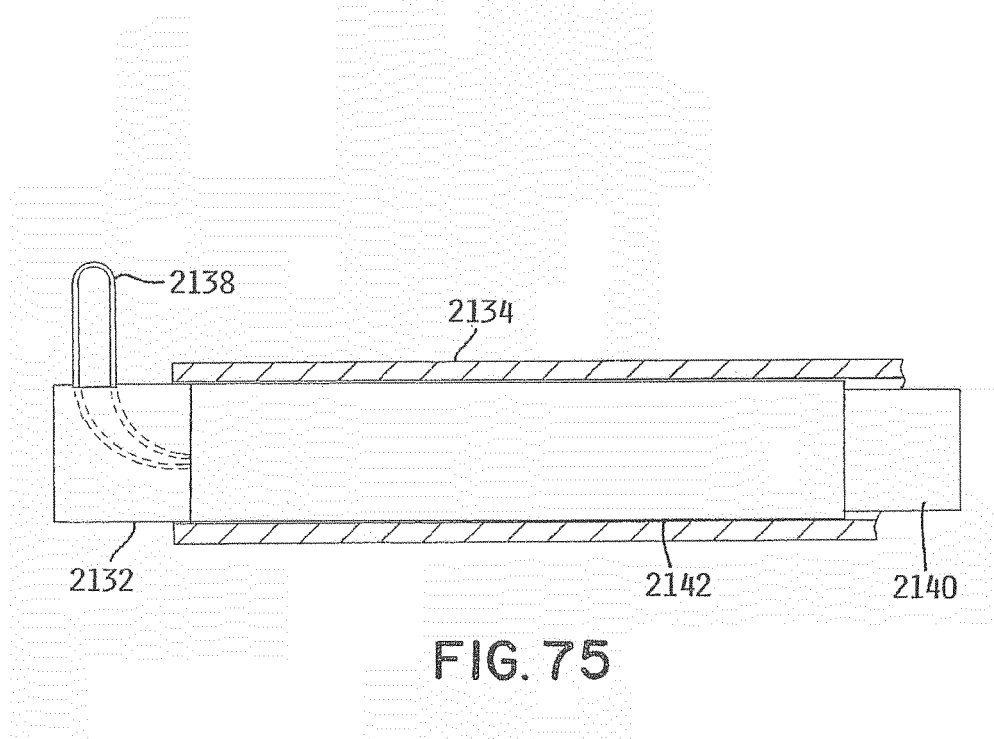
FIG. 75 is a sectional view of the undercutting system of FIG. 74.

Another configuration of the cutting assembly 2132 includes a pre-bent sharpened loop 2138 that is attached to a control rod 2140, as illustrated in FIGS. 74 and 75. The control rod 2140 is slidably mounted in an outer tube 2142. The outer tube 2142 has an opening formed therein proximate a distal end thereof. The opening is configured to allow the pre-bent sharpened loop 2138 to extend therefrom.

In an initial configuration, the pre-bent sharpened loop 2138 is substantially retained within the control rod 2140 so that the cutting assembly 2132 may be inserted into the cannula 2134.

Once the distal end of the cutting assembly 2132 is positioned between the ilium and the sacrum, the pre-bent sharpened loop 2138 may be progressively extended from the outer tube 2142. Extension and retraction of the pre-bent sharpened loop 2138 may be controlled using a variety of techniques. In one technique, the control rod 2140 slides with respect to the outer tube 2142 such that sliding of the control rod 2140 causes the pre-bent sharpened loop 2138 to slide.

As an alternative to advancing both ends of the pre-bent sharpened loop 2138 at the same rate, it is possible to advance only one of the ends of the pre-bent sharpened loop 2138 when moving the cutting assembly 2132 from the retracted configuration to the extended configuration.

If a distal end of the cutting assembly 2132 engages a surface that the cutting assembly 2132 cannot cut through and the operator continues to rotate the cutting assembly 2132, it is possible that the cutting assembly 2132 may break. Breakage of the cutting assembly 2132 when positioned between the ilium and the sacrum may present challenges to the extraction of the components of the cutting assembly 2132 through the cannula. For example, it may be necessary for a larger aperture to be formed in the ilium to extract the broken components. Such a larger aperture would negatively impact the patient's ability to recover from the surgery.

To minimize the potential of the cutting assembly 2132 breaking during the cutting process, a clutch mechanism may be provided between the handle and the cutting assembly 2132. The clutch mechanism causes the operable connection between the handle and the cutting assembly 2132 to release when greater than a threshold force is encountered. When this occurs, the handle rotates with respect to the cutting assembly 2132.

An audible notification may be provided to indicate to the person operating the cutting assembly 2132 that the clutch has been engaged. An example of which such audible notification is a scratching sound that is sufficiently loud to be heard outside of the patient.

After the clutch has been activated, the person operating the cutting assembly 1832 may rotate the cutting assembly 2132 in an opposite direction or partially retract the cutting assembly 2132. Thereafter, the cutting process may be resumed.

Another configuration of the undercutting system is illustrated in FIGS. 76-81. A feature of this undercutting system is that it includes a detachable cutting assembly 2232. The detachable cutting assembly 2232 enables the undercutting system to be reconfigured for different aspects of preparing the surfaces of the ilium and the sacrum for the sacroiliac fusion process. The detachable cutting assembly 2232 may also be replaced if it becomes dull or damaged in use.

The undercutting system includes an outer shaft 2234 positioned with respect to a rotation handle 2272. Rotating the rotation handle may rotate the undercutting system. An advancement handle 2236 is positioned in the proximal end of the rotation handle 2272. Rotating the advancement handle 2236 enables external threads 2274 on the advancement handle 2236 to interface with the internal threads 2276 on the rotation handle 2272 permitting attachment and variable position adjustment of the advancement handle 2236 with respect to the rotation handle 2272 and outer shaft 2234.

The cutting assembly guide 2230 may have a distal portion with a diameter that is approximately the same as an outer diameter of the outer shaft 2234, while the proximal portion has a diameter that is approximately the same as the inner diameter of the outer shaft 2234. Using such a configuration enables a proximal portion of the cutting assembly guide 2230 to be inserted into the outer shaft 2234 until reaching the stepped shoulder on the distal portion of the cutting assembly guide 2230.

The cutting assembly guide 2230 has a channel 2240 extending therethrough. The channel 2240 may have a height and a width that are both slightly larger than a height and a width of the cutting assembly 2232. Using such a configuration enables the cutting assembly 2232 to slide with respect to the cutting assembly guide 2230.

The channel 2240 includes a proximal channel portion 2242 and a distal channel portion 2244 that are in communication with each other. The proximal channel portion 2242 may be generally aligned with a central axis of the cutting assembly guide 2230 while being offset along a surface of the cutting assembly guide 2230. In such a configuration, the outer shaft 2234 extends over the open edge of the proximal channel portion 2242 to thereby retain the cutting assembly 2232.

The distal channel portion 2244 is curved to change from an orientation generally parallel to the central axis of the cutting assembly guide 2230 to an orientation generally perpendicular to the central axis. The distal channel portion 2244 thereby deflects the cutting assembly 2232 to an orientation such that the cutting assembly can extend between the ilium and the sacrum to remove cartilage therefrom.

The radius of curvature of the distal channel portion 2244 depends on the space available and the flexibility of the cutting assembly 2232. If the cutting assembly 2232 is highly flexible, the radius can be relatively small. On the other hand, if the cutting assembly 2232 is less flexible, the radius will need to be larger.

A variety of techniques may be used for connecting the cutting assembly 2232 to an advancement handle 2236 on the outside of the undercutting system to enable the cutting assembly 2232 to move from a retracted position to an extended position. One suitable connection mechanism utilizes a connector head 2252. The connector head 2252 may or may not be permanently attached to the advancement handle 2236 or the cutting assembly 2232.

In one configuration, the connector head 2252 includes a ball mechanism 2254 extending from an end thereof. The advancement handle 2236 has a ball shaped recess 2256 formed therein. The ball mechanism 2254 may have a diameter that is slightly smaller than a diameter of the ball shaped recess 2256.

The ball mechanism 2254 may be placed in the ball shaped recess 2256 from a side thereof. Using such a configuration enables the connector head 2252 to be detached from the advancement handle 2236 when the ball mechanism 2254 and the ball shaped recess 2256 are not in the outer shaft 2234. When the ball mechanism 2254 and the ball shaped recess 2256 are both within the outer shaft 2234, the connector head 2252 is retained in engagement with the advancement handle 2236.

The use of the preceding mechanism for operably attaching the advancement handle 2236 and the connector head 2252 enables the advancement handle 2236 to rotate with respect to the connector head 2252 without the connector head 2252 rotating.

An end of the connector head 2252 opposite the ball mechanism 2254 may include a recess 2260 that is adapted to receive a portion of the cutting assembly 2232 for operably attaching the cutting assembly 2232 to the connector head 2252.

In certain embodiments, the connector head 2252 has a pin 2262 extending therefrom and an aperture 2264 is formed in an end of the cutting assembly 2232. This configuration operably connects the cutting assembly 2232 and the connector head 2252 when these components are in the outer shaft 2234.

The connector head 2252 may have a generally cylindrical shape with an outer diameter that is slightly smaller than an inner diameter of the outer shaft 2234 so that the connector head 2252 may be positioned within the outer shaft 2234.

A proximal end of the advancement handle 2236 may have a gripping surface 2270 formed thereon to enhances the ability of the operator to manipulate the advancement handle 2236. The gripping surface 2270 may have a variety of surface textures and a diameter greater than the distal diameter of the advancement handle 2236.

A distal end of the advancement handle 2236 may have a generally cylindrical shape that is slightly smaller than an inner diameter of the outer shaft 2234 so that it may be positioned within the outer shaft 2234.

A rotation handle 2272 may be positioned over a proximal end of the outer shaft 2134. The rotation handle 2272 may have a diameter that is greater than a diameter of the gripping surface 2270 of the advancement handle 2236. Forming these surfaces with different diameters reduces the potential of the operator engaging both of the surfaces when it is intended to grip only one of the surfaces.

The rotation handle 2272 may be used for rotating the undercutting system once the undercutting system is moved to an extended position between the ilium and the sacrum. Increasing the diameter of the rotation handle 2272 thereby increases the torque that may be applied to cause the undercutting system to cut through the cartilage between the ilium and the sacrum.

A torque limiting device may be included in the components of the undercutting system. The torque limiting device may protect the cutting assembly 2232 from breaking in response to a sufficiently large rotational force being placed on the cutting assembly 2232. A person of skill in the art will appreciate that the torque limiting device may take a variety of configurations.

The undercutting system may also include an auto advancing system that causes the advancement handle 2236 to advance automatically in response to rotation of the rotation handle 2272. This would cause the cutting head to move further into the region between the ilium and the sacrum in response to rotation of the undercutting system. A person of skill in the art will appreciate that a variety of techniques may be used to fabricate the auto advancing system.

The cutting assembly 2232 may be formed with a round or square profile that conforms to the profile of the channel 2240. The cutting assembly 2232 may include a tip portion 12280 having at least one sharpened edge.

Such a configuration provides the tip portion 2280 with flexibility along a distal—proximal direction while providing the tip portion 2280 with rigidity along a radial—tangential direction. The distal—proximal flexibility enables the cutting assembly 2232 to conform to surfaces of the ilium and the sacrum that are not flat and/or perpendicular to the axis of the undercutting system. The radial—tangential rigidity enables the cutting assembly 2232 to cut cartilage as the undercutting system is rotated.

A length of the tip portion 2280 may be selected based upon a size of the ilium and the sacrum that must be prepared by removing the cartilage from therebetween. Minimizing the length of the tip portion 2280 may be desirable to reduce the cost of the cutting assembly 2232, as the tip portion 2280 may be more expensive than the other portions of the cutting assembly 2232.

An end 2282 of the tip portion 2280 may not include a sharpened surface. Forming the end 2282 with such a configuration reduces the potential of undesirable cutting as the cutting assembly 2232 is being inserted into the region between the ilium and the sacrum. As illustrated in FIG. 80, the end 2282 may be curved such as in a semi-circular shape.

The tip portion 2280 may have an oscillating configuration that is at least partially in a sinusoidal shape. A variety of techniques may be used to fabricate the cutting assembly 2232 with such a shape. For example, the loops may be cut into a straight piece of material. Alternatively, a straight piece of material may be bent to form the loops. The material from which the cutting assembly is fabricated may play a role in determining the technique used to fabricate the cutting assembly 2232. Suitable materials for the cutting assembly 2232 may include stainless steel, nitinol, and elgiloy.

Figure 82:
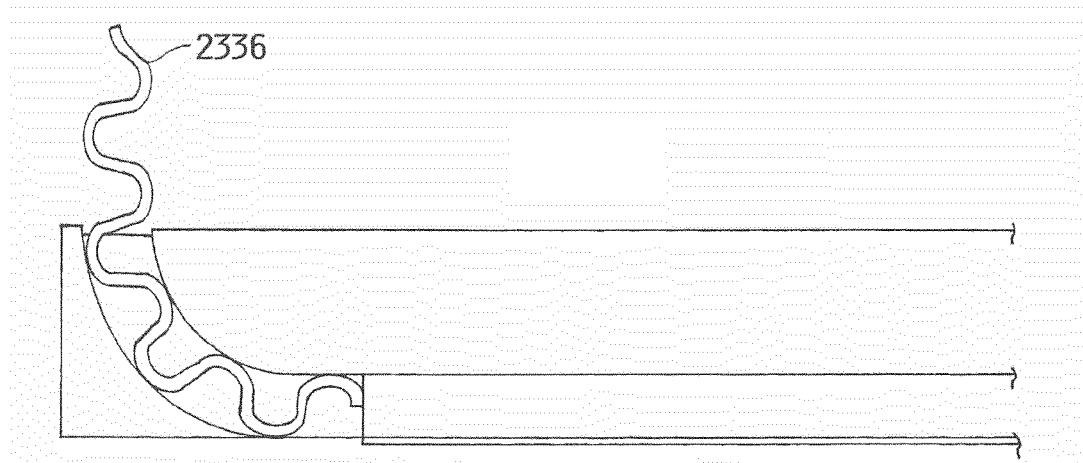
FIG. 82 is a sectional view of an alternative configuration of the undercutting system where a cutting assembly is in an extended configuration.

Another configuration of the undercutting system is illustrated in FIG. 82. This embodiment of the undercutting system is similar to the embodiment illustrated in FIGS. 76-81 except that an end of the cutting head 2336 is outwardly directed. Such a configuration may assist in forming an initial hole in the cartilage prior to rotation of the undercutting system.

Figure 83:
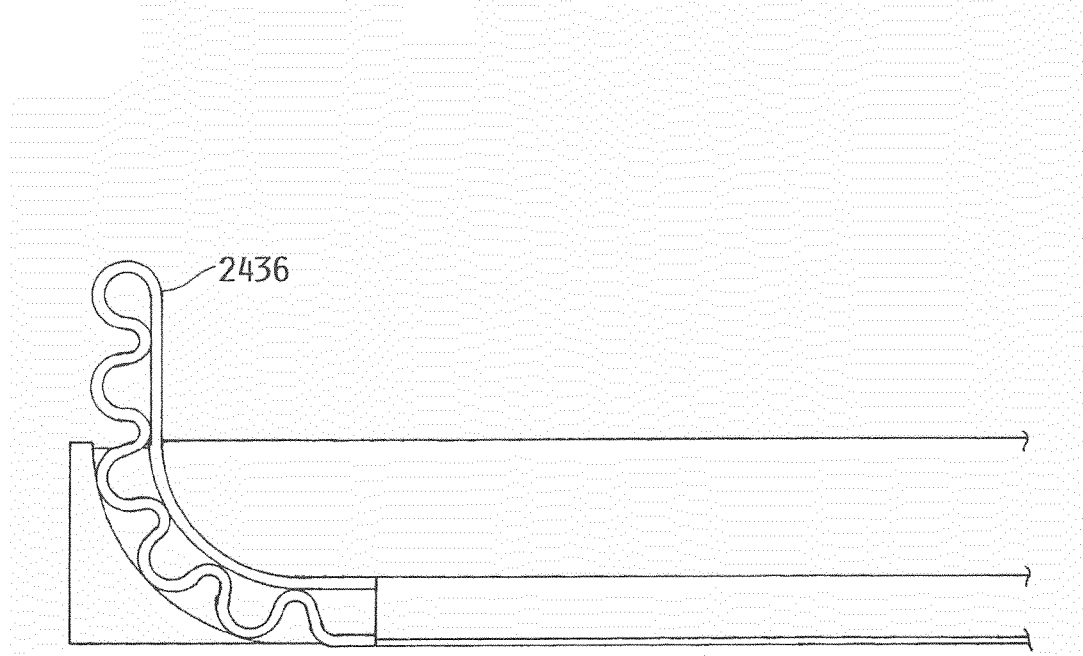
FIG. 83 is a sectional view of an alternative configuration of the undercutting system where a cutting assembly is in an extended configuration.

Another configuration of the undercutting system is illustrated in FIG. 83. This embodiment of the undercutting system is similar to the embodiment illustrated in FIGS. 76-81 except that an end of the cutting head 2436 is in the shape of a loop and a portion of the cutting head 2336 extends behind the oscillating portion of the cutting head 2436. This configuration may provide additional rigidity to the cutting head 2436 when rotating to cut the cartilage between the ilium and the sacrum.

Figure 84:
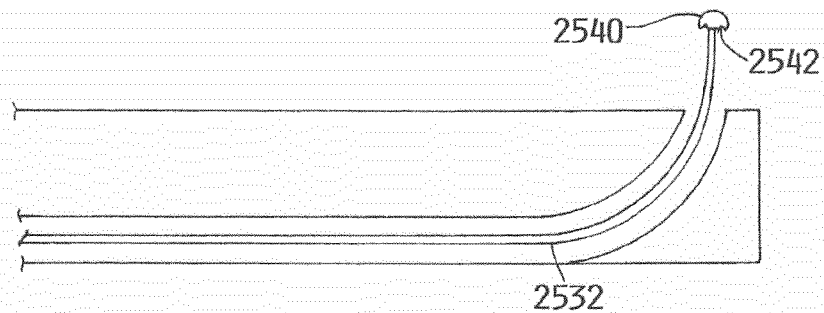
FIG. 84 is a sectional view of an alternative configuration of the undercutting system where a cutting assembly is in an extended configuration.
Figure 85:
FIG. 85 is a sectional view of a guide head for use on the cutting assembly of FIG. 84.
Figure 86:
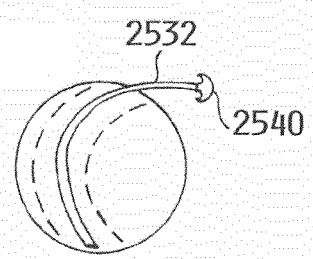
FIG. 86 is an end view of the undercutting system of FIG. 84.

Another configuration of the undercutting system is illustrated in FIGS. 84-86. This embodiment includes an undercutting guide similar to the embodiment illustrated in FIGS. 76-81. The cutting assembly 2532 is formed from a relatively rigid wire such as nitinol.

A cutting cap 2540 is attached to a distal end of the wire. The cutting cap 2540 may have a relatively smooth curved distal surface, as illustrated in FIG. 85. A proximal surface of the cap may include a sharpened edge 2542.

Using this configuration of the undercutting system, the wire could be pushed and rotated to advance the cutting cap. Rotation of the undercutting system causes the sharpened edge 2542 to engage and cut the cartilage. During this rotating process, the wire may bend as illustrated in FIG. 86. Such a bending motion enhances the ability of the sharpened edge to cut the cartilage.

Figure 87:
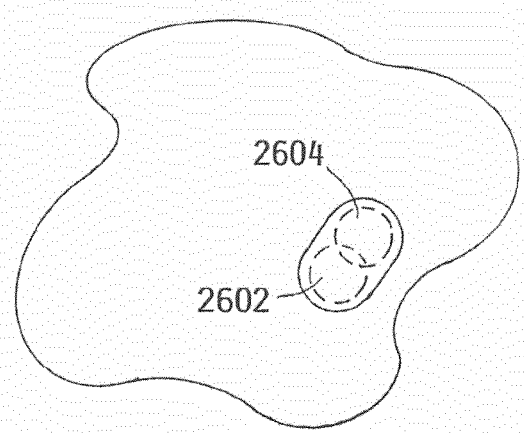
FIG. 87 is a top view of an alternative aperture configuration formed in the ilium.
Figure 88:
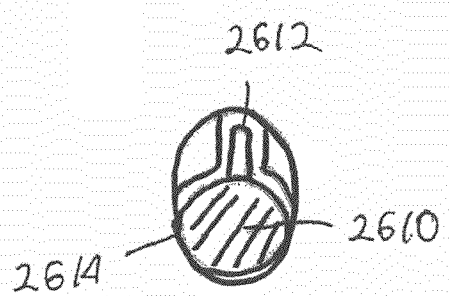
FIG. 88 is a top view of an undercutting system used in conjunction with the aperture of FIG. 87.

Another configuration of the undercutting system involves forming two offset apertures 2602, 2604 in the ilium, as illustrated in FIG. 87. The apertures 2602, 2604 partially overlap such that the apertures form an oblong aperture. The oblong aperture is adapted to receive a similarly shaped oblong cannula 2614. The oblong aperture is also adapted to receive an undercutting system having a shaft 2610 with a cutting head 2612 extending laterally there from, as illustrated in FIG. 88.

This configuration of the undercutting system enables the cutting head 2612 to be either fixedly mounted or partially advanced from the shaft 2610 so to minimize issues with the cutting head 2612 advancement with respect to the shaft 2610. As the shaft 2610 is rotated, it may be necessary to move a rotational axis of the shaft 2610 from one side of the oblong cannula 2614 to another, so that the inner surface of the ilium all around the aperture 2602, 2604 is prepared for the sacroiliac fusion.

Depending on a thickness of the cutting head 2612, it may be necessary to move the shaft axially so that an upper end of the cutting head 2612 contacts the inner surface of the sacrum to prepare that surface for the sacroiliac fusion.

Figure 89:
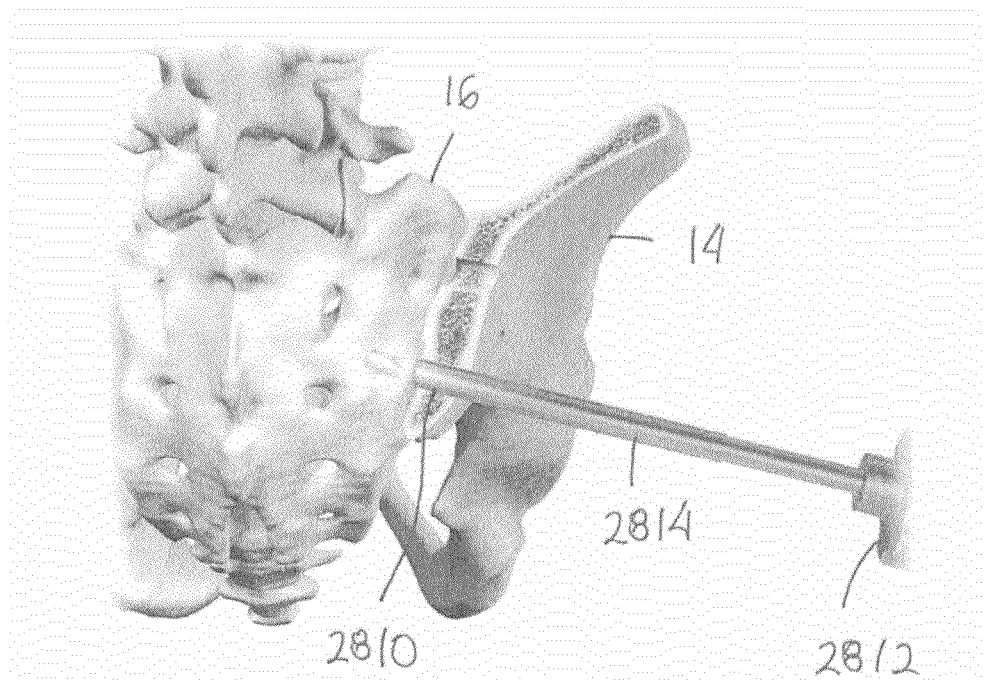
FIG. 89 is a partially cut away perspective view of an aperture being drilled in the sacrum and the ilium as an initial step in a sacroiliac fusion procedure.

In operation, after appropriate preparation of the patient and identification of the location for the sacroiliac fusion, at least one aperture 2810 is drilled through the ilium 14 and at least partially into the sacrum 16, as illustrated in FIG. 89. In certain embodiments, there are three apertures drilled.

A conventional surgical drill 2812 and drill bit 2814 may be utilized to form the aperture 2810. The aperture 2810 may be formed with a diameter that is selected based upon a diameter of the bone screw 2820 that will be inserted into the aperture 2810 as part of the sacroiliac fusion process.

Figure 90:
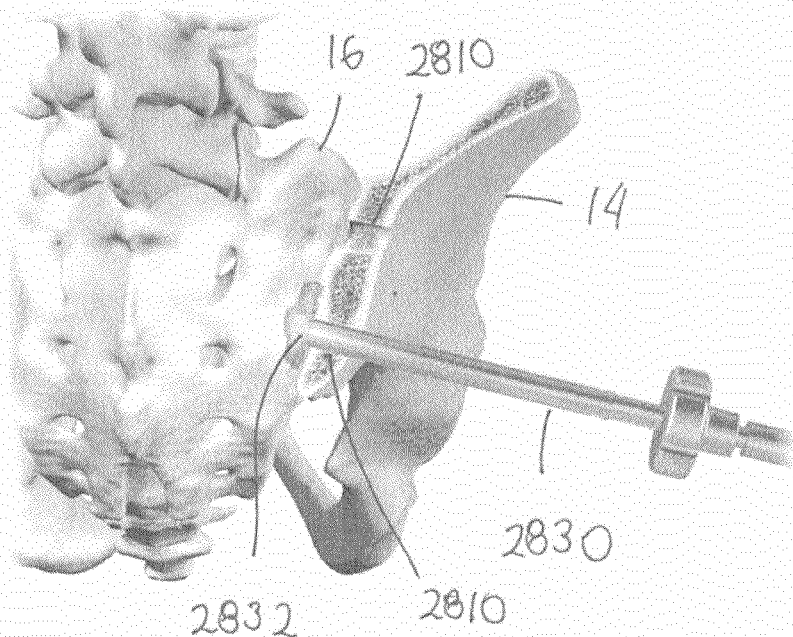
FIG. 90 is a partially cut away perspective view of an undercutting system being inserted into the aperture.

Next, the undercutting system 2830 is positioned in a retracted configuration so that the cutting assembly 2832 does not interfere with the insertion process. The distal end of the undercutting system 2830 is extended into the aperture 2810, as illustrated in FIG. 90.

Figure 91:
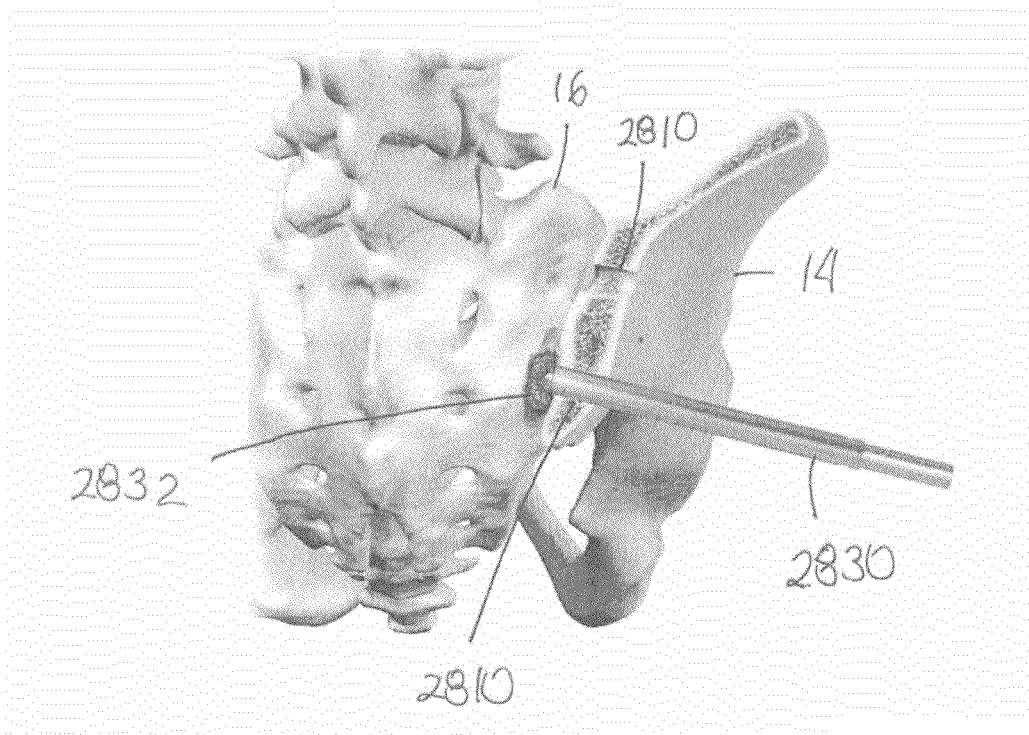
FIG. 91 is a partially cut away perspective view of the undercutting system being used to form an undercut region between the sacrum and the ilium.

Once the distal end of the undercutting system 2830 is positioned between the ilium 14 and the sacrum 16, as illustrated in FIG. 91, the cutting assembly 2832 is moved to an at least partially extended configuration. The undercutting system 2830 is rotated to cause cartilage between the ilium 14 and the sacrum 16 that is in the path of the cutting assembly 2832 to be cut up.

Contact between the cutting assembly 2832 and the inner surfaces of the ilium 14 and the sacrum 16 causes the respective surfaces to be abraded to create bleeding bone, which is needed to facilitate bone growth between the ilium 14 and the sacrum 16 as part of the sacroiliac fusion process.

A technique is then utilized to remove the bits of cartilage and other tissue from between the ilium 14 and the sacrum 16. One suitable apparatus that may be used for remove the bits of cartilage and other tissue is a radial deployment surgical tool, which is described in US Applic. No. 61/349,303, which was filed with the U.S. Patent & Trademark Office on May 28, 2010, and which is assigned to the assignee of the present patent application.

Figure 92:
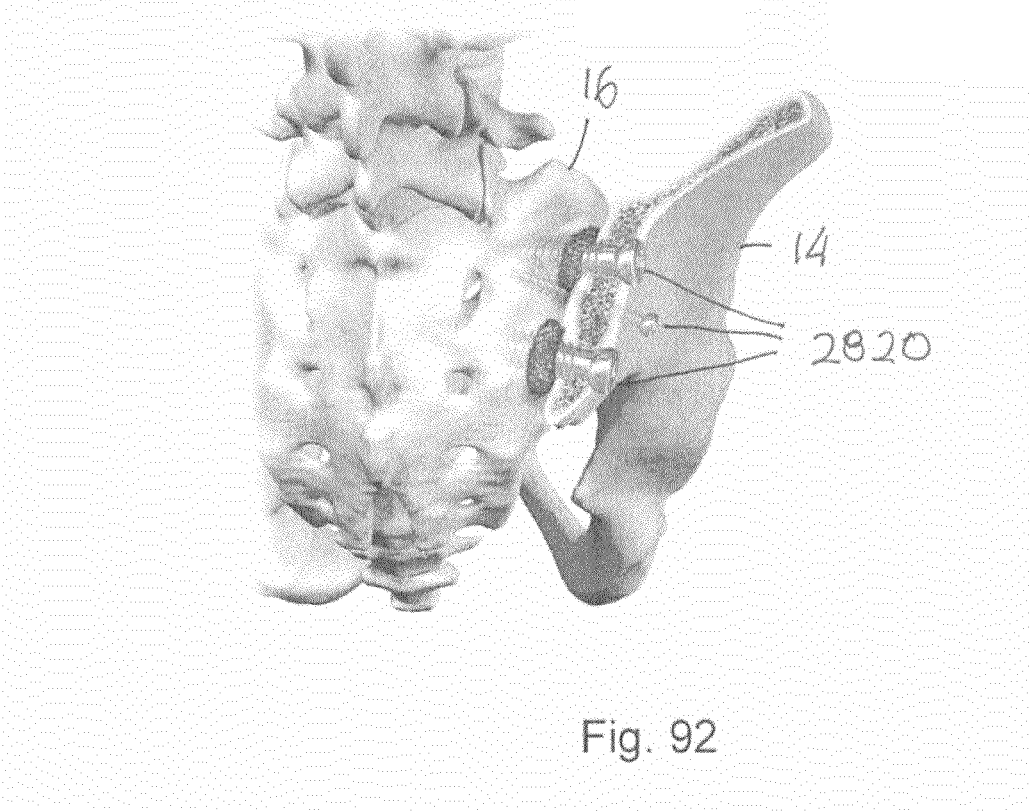
FIG. 92 is a partially cut away perspective view of fasteners inserted into the apertures.

Thereafter, bone screws 2820 may be inserted into each of the apertures 2810, as illustrated in FIG. 92. The bone screws 2820 will be effective at maintaining the ilium 14 and the sacrum 16 in a stationary position with respect to each other as bone grows there between to cause fusion of the ilium 14 and the sacrum 16.

While the figures only illustrated the procedure being performed on one side of the patient, a person of skill in the art will appreciate that the process may be repeated on the other side of the patient.

Depending on a variety of factors such as the sharpness of the cutting head and the hardness of the material being cut, it may not be possible to merely cut through the cartilage and bone using just a rotational motion. Rather, it may be necessary to alternate rotate the undercutting system in clockwise and counter clockwise directions to increase the area that is prepared. While in many circumstances, it may be desirable to prepare a circular area, it is also possible to use the concepts of the invention to prepare a semi-circular area.

A variety of techniques may be used to evaluate the amount of cartilage that has been removed and the extent to which the surfaces of the ilium and the sacrum have been prepared. Examples of such suitable techniques include monitoring the sound emitted during the cutting process, as the cutting of bone may make a scraping sound.

The person operating the undercutting system may monitor the performance of the process using the feel of the cutting head, as it may be more difficult for the cutting head to cut through the ilium and the sacrum than the cartilage.

It is also possible to monitor the progress of the preparation for the sacroiliac fusion using a fluoroscope. While these techniques are described individually, it is possible for one or more of the preceding techniques to be combined.

After a desired amount of cartilage between the ilium and the sacrum has been cut up to prepare for the sacroiliac fusion, it may be desirable to remove the cut up bits of cartilage from between the ilium and the sacrum to facilitate bone growth between the ilium and the sacrum.

One technique for removing the cut up bits of cartilage is to flush the region with a fluid and then suction out the water with the cut up bits of cartilage. The process may be repeated until a desired amount of the cut up bits of cartilage is removed from between the ilium and the sacrum.

Another technique for removing the cut up bits of cartilage from between the ilium and the sacrum involves using a clean-up tool. The clean-up tool may include a handle and a plurality of bristles.

After the surfaces of the ilium and the sacrum have been prepared, a bone graft may be inserted. Then, a variety of techniques may be used to maintain the ilium and the sacrum in a fixed position with respect to each other. Examples of suitable fixation techniques include bone screws, cannulated screws, pins, cages, glue, coupled device with ball and socket and Herbert screws.

While the concepts of the invention are primarily described in conjunction with preparation for a sacroiliac fusion, a person of skill in the art will appreciate that the concepts may be adapted for other joints in the body. The concepts may also be used for preparing an interior region of a bone.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of cutting tissue between a first bone and a second bone, wherein the method comprises:
   forming an aperture through the first bone, wherein the aperture has a radius;
   providing an undercutting system, wherein the undercutting system comprises a cutter;
   extending the undercutting system into the aperture;
   moving the cutter with respect to the undercutting system to an extended configuration where at least a portion of the cutter extends from the undercutting system;
   using the cutter to cut tissue between the first bone and the second bone that is beyond the radius of the aperture; and
   removing the undercutting system from the aperture.

2. The method of claim 1, and further comprising positioning the cutter in a refracted configuration where the cutter is within the undercutting system before the undercutting system is extended into the aperture.

3. The method of claim 2, wherein the undercutting system further comprises a control portion and wherein the method further comprises moving the cutter between the refracted configuration and the extended configuration with the control portion.

4. The method of claim 1, and further comprising cutting at least one of the first bone and the second bone with the cutter to form bleeding bone.

5. The method of claim 1, wherein as the cutter moves to the extended configuration, the cutter slides with respect to the undercutting system.

6. The method of claim 1, wherein the undercutting system further comprises an insertion apparatus to which the cutter is attached, wherein the insertion apparatus has a central axis, wherein when the cutter is in the extended configuration, a distal end of the cutter is further from the central axis than when the cutter is in a retracted configuration.

7. The method of claim 6, wherein when moving between the retracted configuration and the extended configuration, a distal end of the cutter moves generally transverse to the central axis.

8. The method of claim 6, wherein the insertion apparatus comprises a guide channel extending between the proximal end and the distal end thereof, wherein proximate the proximal end, the guide channel is aligned substantially parallel to the central axis of the insertion apparatus, wherein proximate the distal end, the guide channel is substantially transverse to the central axis and wherein intermediate the proximal end and the distal end, the guide channel comprises a transition region.

9. The method of claim 1, wherein at least a portion of the cutter is flexible.

10. The method of claim 1, wherein the cutter is detachably attached to the undercutting system.

11. The method of claim 1, wherein cutter comprises a first cutter and a second cutter and wherein the second cutter is sharper than the first cutter.

12. The method of claim 11, wherein the second cutter has a thickness that is greater than a thickness of the first cutter.

13. The method of claim 1, and further comprising:
   removing the cut tissue from between the first bone and the second bone; and
   inserting bone graft material between the first bone and the second bone from where the cut tissue has been removed.

14. The method of claim 13, wherein removing the cut tissue comprises flushing with water.

15. The method of claim 1, and further comprising inserting a fixation device into the aperture, wherein the fixation device engages the first bone and the second bone to retain the first bone and the second in a stationary position with respect to each other.

16. The method of claim 1, wherein the first bone is an ilium and wherein the second bone is a sacrum.

17. The method of claim 1, and further comprising operably attached the cutter to the undercutting system with a torque limiting device.

18. The method of claim 17, wherein the torque limiting device emits an audible notification when the torque limiting device is engaged.

19. The method of claim 1, wherein the cutter cuts in at least one of a reciprocating motion and a rotating motion.

20. A method of cutting tissue between a first bone and a second bone, wherein the method comprises:
   forming an aperture through the first bone, wherein the aperture has a radius;
   providing an undercutting system, wherein the undercutting system comprises an insertion apparatus and a cutter operably attached to the insertion apparatus, wherein the insertion apparatus has a central axis;
   extending an undercutting system into the aperture;
   moving the cutter with respect to the undercutting system to an extended configuration where at least a portion of the cutter extends from the undercutting system, wherein when the cutter is in the extended configuration, a distal end of the cutter is further from the central axis than when the cutter is in a retracted configuration;
   using the cutter to cut tissue between the first bone and the second bone that is beyond the radius of the aperture; and
   removing the undercutting system from the aperture.

21. The method of claim 20, wherein when moving between the retracted configuration and the extended configuration, a distal end of the cutter moves generally transverse to the central axis.

22. A method of cutting tissue between a first bone and a second bone, wherein the method comprises:
   forming an aperture through the first bone, wherein the aperture has a radius;
   providing an undercutting system, wherein the undercutting system comprises a cutter;
   extending an undercutting system into the aperture;
   moving the cutter with respect to the undercutting system to an extended configuration where at least a portion of the cutter extends from the undercutting system;
   using the cutter to cut tissue between the first bone and the second bone that is beyond the radius of the aperture;
   removing the undercutting system from the aperture;
   removing the cut tissue from between the first bone and the second bone; and
   inserting bone graft material between the first bone and the second bone from where the cut tissue has been removed.

23. The method of claim 22, wherein removing the cut tissue comprises flushing with water.

* * * * *